(12) United States Patent
Anderson et al.

(10) Patent No.: US 7,686,760 B2
(45) Date of Patent: Mar. 30, 2010

(54) TRANSOBTURATOR SURGICAL ARTICLES AND METHODS

(75) Inventors: Kimberly A. Anderson, Eagan, MN (US); Brian P. Watschke, Eden Prairie, MN (US); Georges Mellier, Lyons (FR); Johann J. Neisz, Coon Rapids, MN (US)

(73) Assignee: AMS Research Corporation, Minnetonka, MN (US)

( * ) Notice: Subject to any disclaimer, the term of this patent is extended or adjusted under 35 U.S.C. 154(b) by 1433 days.

(21) Appl. No.: 11/064,875

(22) Filed: Feb. 24, 2005

(65) Prior Publication Data
US 2005/0143618 A1 Jun. 30, 2005

Related U.S. Application Data

(63) Continuation of application No. 10/377,101, filed on Mar. 3, 2003, now Pat. No. 6,911,003, which is a continuation-in-part of application No. 10/306,179, filed on Nov. 27, 2002, now Pat. No. 7,070,556.

(60) Provisional application No. 60/362,806, filed on Mar. 7, 2002, provisional application No. 60/380,797, filed on May 14, 2002, provisional application No. 60/402, 007, filed on Aug. 8, 2002, provisional application No. 60/414,865, filed on Sep. 30, 2002.

(51) Int. Cl.
*A61F 2/02* (2006.01)
(52) U.S. Cl. .......................................... 600/30; 600/37
(58) Field of Classification Search ............. 600/29–32, 600/37
See application file for complete search history.

(56) References Cited

U.S. PATENT DOCUMENTS 6,638,211 B2 * 10/2003 Suslian et al. .................. 600/30

FOREIGN PATENT DOCUMENTS

WO    WO 94/24954    * 11/1994

* cited by examiner

*Primary Examiner*—Charles A Marmor, II
*Assistant Examiner*—Carrie Harris
(74) *Attorney, Agent, or Firm*—Jose' W. Jimenez; Kimberly K. Baxter; Gregory L. Koeller

(57) ABSTRACT

Surgical articles, implants and components suitable for a transobturator surgical procedure are described.

31 Claims, 41 Drawing Sheets

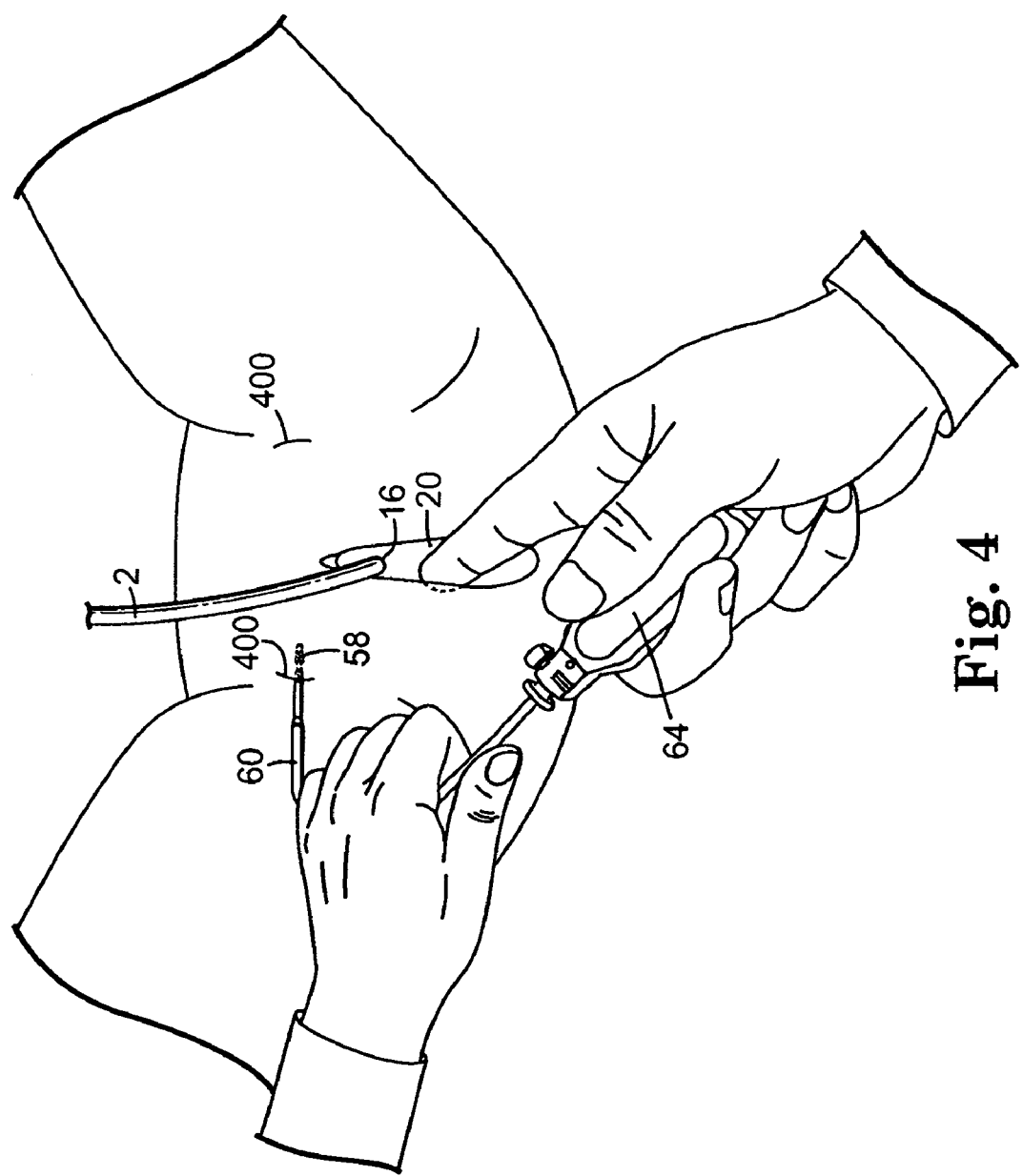

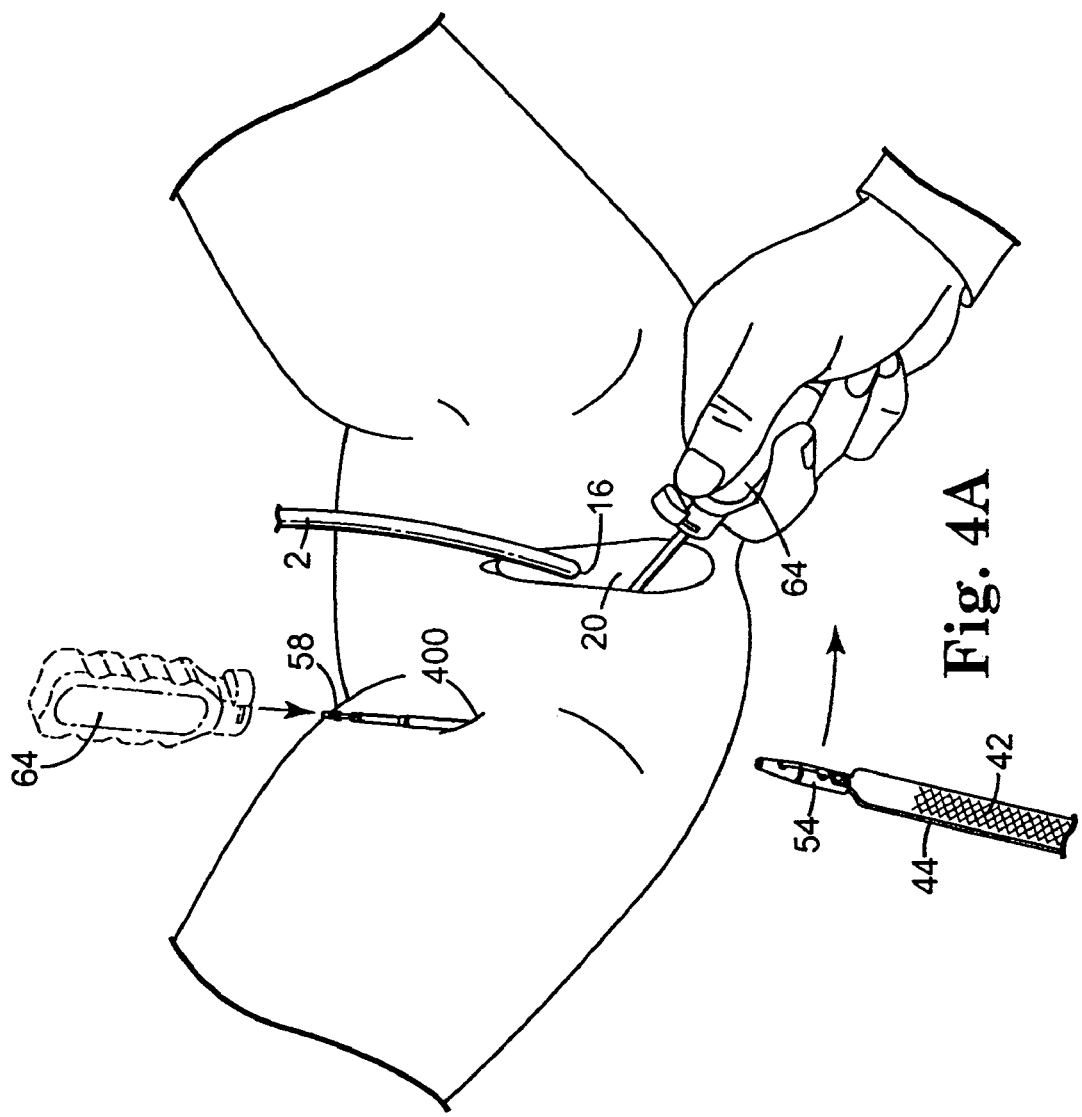

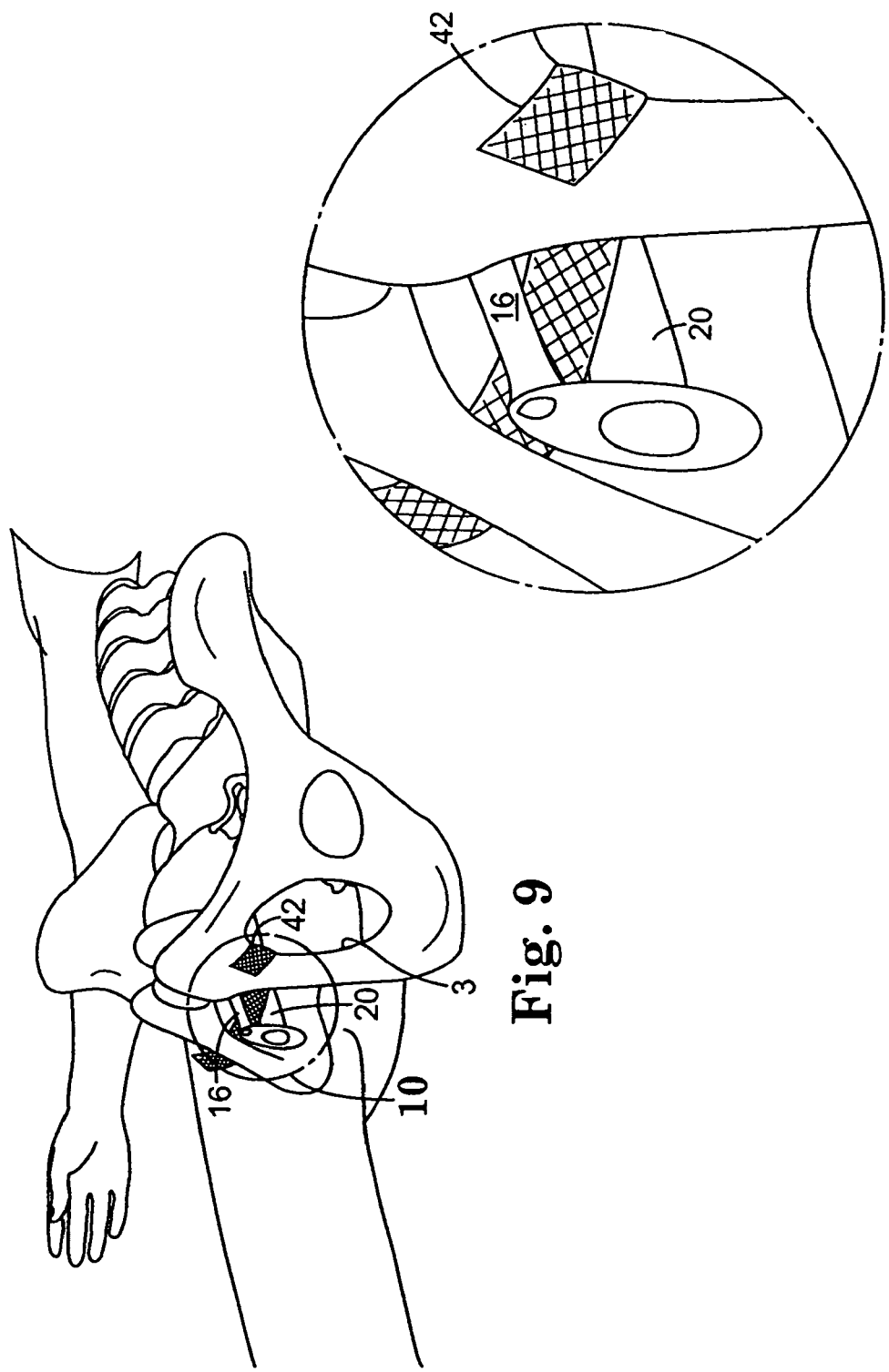

US 7,686,760 B2

TRANSOBTURATOR SURGICAL ARTICLES AND METHODS

CROSS REFERENCE TO RELATED APPLICATIONS

This application is a Continuation of prior U.S. patent application Ser. No. 10/377,101 filed Mar. 03, 2003, now U.S. Pat. No. 6,911,003, which is a Continuation-in-Part of U.S. patent application Ser. No. 10/306,179 filed on: Nov. 27, 2002, now U.S. Pat. No. 7,070,556 which '179 application claims the benefit of U.S. Provisional Applications. Ser. No. 60/362,806 filed Mar. 7, 2002; Ser. No. 60/380,797 filed May 14, 2002; Ser. No. 60/402,007 filed Aug. 8, 2002; and Ser. No. 60/414,865 filed Sep. 30, 2002.

BACKGROUND

Urinary incontinence is a significant health concern worldwide. In the urology field, needles, suture passers and ligature carriers are utilized in a variety of procedures, many of which are designed to treat incontinence. Examples of such surgical instruments included Stamey needles, Raz needles, and Pereyra needles. See Stamey, *Endoscopic Suspension of the Vesical Neck for Urinary Incontinence in Females*, Ann. Surgery, pp. 465-471, October 1980; and Pereyra, *A Simplified Surgical Procedure for the Correction of Stress Incontinence in Women*, West. J. Surg., Obstetrics & Gynecology, pp. 243-246, July-August 1959.

A pubovaginal sling procedure is a surgical method involving the placement of a sling to stabilize or support the bladder neck or urethra. There are a variety of different sling procedures. Descriptions of different sling procedures are disclosed in U.S. Pat. Nos. 5,112,344; 5,611,515; 5,842,478; 5,860,425; 5,899,909; 6,039,686; 6,042,534 and 6,110,101.

Some pubovaginal sling procedures extend a sling from the rectus fascia in the abdominal region, to a position below the urethra, and back again to the rectus fascia. Although serious complications associated with sling procedures are infrequent, they do occur. Complications include urethral obstruction, prolonged urinary retention, bladder perforations, damage to surrounding tissue, and sling erosion.

The Tension-free Vaginal Tape (TVT) procedure (available from Ethicon, of N.J.) utilizes a Prolene™ nonabsorbable, polypropylene mesh. Problems with the TVT procedure are documented in the literature and patents. Problems associated with the TVT procedures and the like are acknowledged and described in PCT publication Nos. PCT WO 00/74613 and PCT WO 00/74594, U.S. Pat. Nos. 6,273,852; 6,406,423; and 6,478,727, and published U.S. Pat. Application Nos. 2002-0091373-A1, 2002-0107430-A1, 2002-0099258-A1 and US-2002-0099259-A1. A cadaver study indicated that the TVT needle is placed in close proximity to sensitive tissue such as superficial epigastric vessels, inferior epigastric vessels, the external iliac vessel and the obturator. See, Walters, Mark D., *Percutaneous SuburethralSlings: State of the Art*, presented at the conference of the American Urogynecologic Society, Chicago (October 2001) and PCT International Publication No. WO 02/26108.

Additional sling procedures are disclosed in Published U.S. Pat Appl. No. US 2001/0018549A1, and PCT Publication Nos. WO 02/39890 and WO 02/069781.

A significant percentage of pubovaginal sling procedures are conducted after previous pelvic surgery. A pubovaginal sling procedure can be particularly challenging if the patient has scarring as a result of previous pelvic surgeries or other anatomical problems. The additional complications presented by significant scarring present surgeons with a greater surgical challenge and may lead some surgeons to forego an otherwise beneficial sling procedure. Unfortunately, this reduces a patient's options for treating incontinence.

Published U.S. Pat. Appl. No. 2002/0099260 discloses an implantable device or tape for use in correcting urinary incontinence. The tape includes sprayed polypropylene fibers that result in a strong implantable device. The tape also has a silicone-coated portion and tapered free ends. The procedure utilizes an Emmet needle that includes an eyelet. To create the eyelet, the distal portion of the Emmet needle is enlarged. A surgical procedure using an Emmet needle is believed to be described in the French publication D. Dargent, S. Bretones, P. George, and G. Mellier, *Pose d'un ruban sous uretral oblique par voie obturatrice dans le traitement de l'incontinence urinaire feminine*, Gynecol. Obstet. Fertil. 2002; 30: 576-582.

In the procedure described in U.S. Pat Appl. No. 2002/0099260, an incision is made in the perineal skin facing the obturator and in the groin. The Emmet needle is first inserted through the cutaneous incision. The Emmet needle is first introduced perpendicular to the perineum for about 15 mm (passing through the internal obturator muscle as far as just outside the ischiopubic branch). The Emmet needle is then allowed to describe its curvature. The free end of the tape is then slipped into the eyelet of the needle. The needle/tape connection is thus reversible as one merely needs to unthread the tape from the eyelet to separate the tape from the needle. Separation of the tape and needle while both are within the body is undesirable as it would require the needle to be repassed through the body.

The needle with the tape extending through the eyelet is then pulled back though the skin incision. The eyelet and threaded tape present a sudden discontinuity encountered by the tissue that can make tape and needle passage inconvenient and unnecessarily irritative or traumatic to tissue. Additionally, the final placement of the sling may not be optimum in this procedure.

SUMMARY OF THE INVENTION

In one aspect, the present invention comprises a novel surgical instrument for treating incontinence. The instrument comprises a handle portion, and a needle portion with a distal region. Unlike the Emmet needle of the prior art, the novel instrument has substantial structure in three dimensions. The needle portion is sized and shaped to extend between an incision substantially adjacent the patient's obturator foramen and a vaginal incision. The needle portion also has structure near the distal region for associating the instrument with an implantable material for treating the incontinence. Preferably, the needle portion includes a portion that is substantially helically shaped, more preferably, it is a variable helix shape. The structure for associating the instrument with an implantable material can comprise an eyelet or a dilator or other structure.

The handle portion is preferably elongate along a handle axis, the needle portion includes a substantially straight spacer portion along the handle axis, and a variable spiral portion extending from the spacer portion. The variable spiral portion preferably has a tissue clearance depth of greater than about 1.5 inches and less than about 2.5 inches, and a maximum width of greater than about 1.25 inches and less than about 3 inches.

In one embodiment, the handle portion is elongate defining a mid plane, and the distal end of the novel needle includes a distal-tip situated substantially near an extension of the mid plane that is spaced from the handle portion.

In another aspect, the present invention comprises a surgical instrument comprising first and second ends, the instrument having a portion that is sized and shaped to extend between a vaginal incision and an incision substantially adjacent the patient's obturator foramen. One of the ends has a handle, at least the other end having securement surfaces for snap fitting the instrument to another surgical component used to treat incontinence. The snap fit preferably provides a substantially permanent attachment between the instrument and the other surgical component. Preferably, the other surgical component comprises a dilator of a sling assembly. The instrument and the dilator preferably have complementary engagement surfaces for resisting separation of the instrument from the dilator once they are snap fitted together.

In another aspect, the novel instrument comprises a handle portion, a needle portion having an extension portion (e.g. a substantially straight portion) projecting from the handle portion and a variable spiral portion with a distal region. The variable spiral portion is sized and shaped to extend between an incision substantially adjacent the patient's obturator foramen and a vaginal incision. The needle portion has structure in the distal region for associating the instrument with an implantable material for treating incontinence.

In yet another aspect, the present invention comprises a surgical assembly for treating incontinence. The assembly includes a surgical instrument having a handle portion, a needle portion having substantial structure in three dimensions and a distal region. The needle portion has a portion that is sized and shaped to extend between an incision substantially adjacent a patient's obturator foramen and a vaginal incision. The assembly may also include an implantable synthetic material and a sheath situated about the implantable synthetic material. In this aspect, the needle portion has structure in the distal region for associating the instrument with the implantable synthetic material. The assembly may further including a dilator. Alternatively, needle may comprise an eyelet.

When the assembly includes a dilator, the dilator preferably has engagement surfaces for connecting the dilator to the instrument. The dilator is preferably operatively associated with the sheath and implantable material. The structure of the needle portion in the distal region comprises surfaces complementary with the engagement surfaces of the dilator for resisting separation of the instrument from the dilator once they are engaged. Preferably, the needle portion is sized and shaped for a predetermined side of a patient, and the handle portion includes indicia indicating the predetermined side of the patient.

In another aspect, the present invention comprises a surgical assembly comprising a first surgical instrument for use on a right side of a patient. The first surgical instrument comprises a handle portion and a needle portion having substantial structure in three dimensions and a distal region. The needle portion has a portion that is sized and shaped to extend between an incision substantially adjacent the obturator foramen on the patient's right side and a vaginal incision. The assembly also has a second surgical instrument for use on a left side of a patient. The second surgical instrument comprises a handle portion and a needle portion having substantial structure in three dimensions and a distal region. The needle portion of the second instrument has a portion that is sized and shaped to extend between an incision substantially adjacent the obturator foramen on the patient's left side and a vaginal incision.

Preferably, the handle portion of the first surgical instrument includes indicia indicating the first surgical instrument is for use on the right side of the patient, and the handle portion of the second surgical instrument includes indicia indicating the second surgical instrument is for use on the left side of the patient. The assembly may also include an implantable knitted polypropylene material, and a sheath situated about the implantable synthetic material. The first and second surgical instruments may include an eyelet for receiving a suture to tie the surgical instrument to the implantable material. Alternatively, the assembly can have first and second dilators for associating the first and second surgical instruments with the implantable material.

In another aspect the present invention comprises a surgical instrument for treating incontinence comprising a needle sized and shaped to either a) initially extend through an incision substantially adjacent a patient's obturator foramen and then through a vaginal incision, or b) initially extend through a vaginal incision and subsequently through an incision substantially adjacent a patient's obturator foramen. Notably, such a surgical instrument need not have substantial structure in three dimensions. Preferably, the needle comprises a pair of ends having surfaces for affording association with either an implantable sling material or a removable handle. In one embodiment, the needle is sized and shaped for use on either the patient's right side or left side.

In another aspect, the present invention comprises methods for treating incontinence. Some methods may utilize substantially three dimensional needles, others need not require three dimension needles and other methods may utilize either three dimensional needles or substantially flat needles or both. One method comprises the steps of creating a vaginal incision, creating an incision substantially adjacent the patient's obturator foramen, providing an elongate surgical instrument comprising first and second regions, with at least one of the regions having securement surfaces, providing a sling assembly having an implantable sling for treating the incontinence, the sling assembly having surfaces complementary to the securement surfaces, passing the instrument between the incisions, then snap fitting the instrument to the sling assembly to provide a substantially permanent attachment between the instrument and the assembly, then passing the implantable material through tissue from the vaginal incision toward the incision substantially adjacent the patient's obturator foramen.

In another aspect a method comprises the steps of creating a vaginal incision, creating an incision substantially adjacent the patient's obturator foramen, providing an elongate surgical instrument comprising first and second regions, the instrument having substantial structure in three dimensions, providing an implant for treating the incontinence, passing the first region between the incisions, then associating the implant with the instrument, and passing the implant through tissue and through the patient's obturator foramen with the instrument. Preferably, the step of providing an elongate surgical instrument includes the step of providing an instrument with a portion that is substantially helically shaped, and the step of passing the implant through tissue includes the step of passing the implant along a substantially three dimensional or helical path. The step of providing an elongate surgical instrument preferably includes the step of providing an instrument with an elongate handle portion having an axis, and the step of passing the instrument between the incisions preferably includes the step of rolling the instrument about the axis of the handle portion.

In another aspect, the method comprises the steps of creating a vaginal incision, creating an incision substantially adjacent the patient's obturator foramen, providing an elongate surgical instrument comprising a handle portion, a needle portion having an extension portion projecting from the handle portion and a variable spiral portion with a distal end, providing an implant for treating the incontinence, passing at least a portion of the variable spiral portion between the incisions by initially passing the distal end through the incision substantially adjacent the patient's obturator foramen and then through the vaginal incision, then associating the implant with a portion of the instrument that has emerged from the vaginal incision, and then moving the distal region of the instrument with the implant associated therewith from the vaginal incision toward the patient's obturator foramen to pass the implant through tissue. Optionally, the step of associating the implant with a portion of the instrument that has emerged from the vaginal incision includes the step of using a suture to tie the implant to an eyelet in the distal region of the needle.

In yet another aspect, the method comprises the steps of creating a vaginal incision, creating an incision substantially adjacent the patient's obturator foramen, providing an elongate surgical instrument comprising first and second regions, providing an assembly having an implant for treating incontinence, initially passing the first region of the instrument initially through the vaginal incision toward the incision substantially adjacent the patient's obturator foramen in a path through the patient's obturator foramen until the first region of the instrument emerges from the incision substantially adjacent the patient's obturator foramen, leaving the second region of the needle projecting from the vaginal incision, then associating the second region of the instrument that projects from the vaginal incision with the assembly, and then moving the instrument out of the patient's body to pass the implant through tissue from the vaginal incision toward the incision substantially adjacent the patient's obturator foramen to place the implant in a therapeutically effective position.

In another aspect, the present invention comprises the ornamental design for a surgical instrument, as shown in FIGS. 39 through 45 and described in the Brief Description of the Drawings. Also, the present invention comprises the ornamental design for a surgical instrument, as shown in FIGS. 46 through 52 and described in the Brief Description of the Drawings.

BRIEF DESCRIPTION OF THE DRAWINGS

Other features and advantages of the present invention will be seen as the following description of particular embodiments progresses in conjunction with the drawings, in which:

FIGS. 4 through 10 are schematic views sequentially showing a surgical procedure in accordance with one aspect of the present invention, wherein:

FIG. 4 shows a needle just passing an incision on the right side of a patient's body with the tip of the needle shown in dotted lines;

FIG. 4A is a schematic view of an alternate approach, presented as an alternative to the step shown in FIG. 4, showing an inside-out approach using the needle of FIG. 1, which may be preferred by some surgeon's whose dominant hand is the right hand, the handle shown being a detachable handle that is movable from one region of the needle to the other, with solid lines being used to show the initial position of the handle and dashed lines and an arrow used to show a second position of the handle;

FIG. 5 illustrates a needle just passing an incision on the left side of a patient's body with the tip of the needle and part of the surgeon's finger shown in dotted lines;

FIG. 6 illustrates one side of a sling assembly and the needle of FIG. 5 as it emerges from the patient's vagina;

FIG. 7 shows the sling system of FIG. 6 after it is attached to the needle of FIG. 6;

FIG. 8 is a perspective view of a sling assembly being pulled through the body by a needle in accordance with the present invention, FIG. 9 is a schematic view of the approximate relative positions of the pubic bone and the sling after the sling is inserted according to one aspect of the present invention;

FIG. 10 is an enlarged schematic view showing portions of FIG. 9;

FIGS. 34 through 38 are perspective views sequentially showing a surgical procedure in accordance with another aspect of the present invention, wherein:

FIG. 34 shows a needle just passing an incision on the right side of a patient's body with the tip of the needle shown in dotted lines;

FIG. 35 illustrates a needle just passing an incision on the left side of a patient's body with the tip of the needle and part of the surgeon's finger shown in dotted lines;

FIG. 36 illustrates one side of a sling assembly and the needle of FIG. 35 as it emerges from the patient's vagina;

FIG. 37 shows the sling assembly of FIG. 36 after it is attached to the needle of FIG. 36;

FIG. 38 is a perspective view of a sling assembly being pulled through the body by a needle in accordance with the present invention;

FIGS. 55-57 sequentially illustrate use of the system of FIG. 54 wherein:

FIG. 55 illustrates passage of the needles using inside-out approaches,

FIG. 56 illustrates the needles after the handles have been removed, in preparation for attachment of a sling assembly on the regions of the needles previously occupied by the handles;

FIG. 57 illustrates the system during implantation of the sling;

FIGS. 59-61 sequentially illustrate the system of FIG. 54 used in outside-in approaches wherein:

FIG. 59 illustrates the needles inserted initially through the patient's skin and thereafter emerging from a vaginal incision;

FIG. 60 illustrates the system just prior to attachment of a sling assembly;

FIG. 61 illustrates the system of FIG. 54 during implantation of the sling;

The broken line showing of structures on the design of the surgical instruments in FIGS. 39 through 52 are for illustrative purposes only and form no part of the claimed design.

DETAILED DESCRIPTION

The following description is meant to be illustrative only and not limiting. Other embodiments of this invention will be apparent to those of ordinary skill in the art in view of this description.

The present invention is directed to surgical instruments, assemblies and implantable articles for treating pelvic floor disorders such as incontinence or stress urinary incontinence (SUI) in both men and women. The present invention is also directed to improved surgical procedures that utilize the surgical articles.

Figure 1:
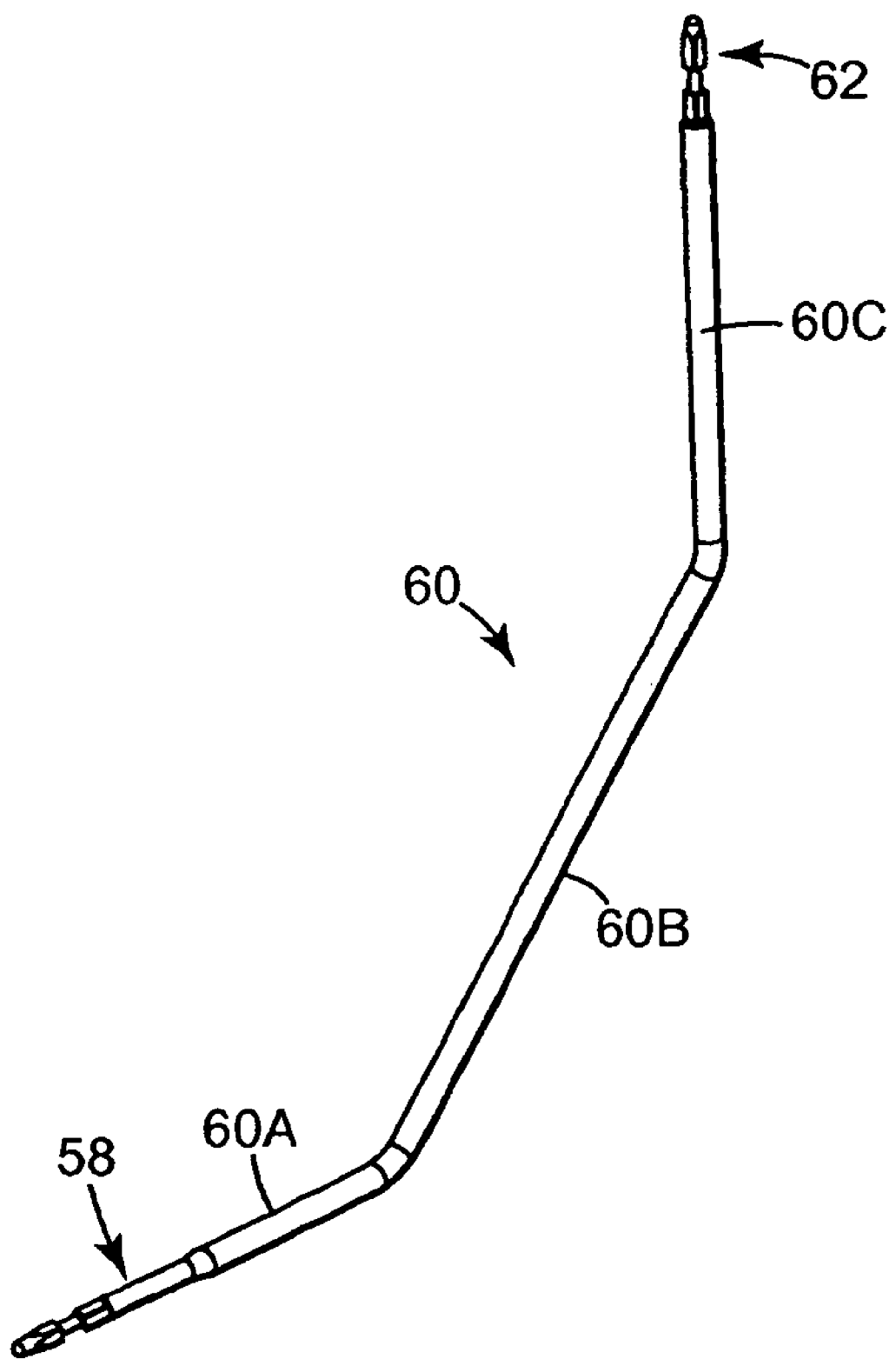
FIG. 1 is a side view of a surgical needle according to one aspect of the present invention.

FIG. 1 is a side view of a sling assembly guide or needle 60 according to one aspect of the present invention. The needle 60 is preferably sized and shaped to be suitable for initial insertion through obturator fascia (see FIGS. 4 through 8). The needle 60 has a length sufficient to extend from the initial incision 400 adjacent the anterior side of the pubic bone, through the obturator foramen 3 (e.g. see FIG. 9) portion of the pubic bone to a position on the posterior side of the pubic bone, and to then emerge from a vaginal incision. While FIG. 1 is a side view or a species of the present invention, the present invention is not limited to the particular shape disclosed. It is expressly understood that a large number of different sizes, shapes and dimensions of needles are suitable for the present invention.

There are many vulnerable, sensitive pelvic anatomical structures and tissues in the region of the obturator foramen 3, including the pudendal artery (internal), the pudendal canal (Alcock), and nerves (e.g. the perineal and labial). The needle 60 is preferably sized and shaped to pass through the obturator foramen 3 along a path that is substantially free of vascular and nerve structures. The size and shape of the needle 60 help avoid the sensitive structures. For example, in one embodiment, the path maybe in a region between the superior pubic ramus and the inferior pubic ramus (see e.g. FIGS. 4 through 10). The tip of the needle is preferably substantially blunt to help avoid damage to the sensitive structures. Alternatively, the tip may be slightly sharpened to assist in the initial passage of the needle.

Preferably, the needle 60 comprises three substantial linear portions 60A, 60B and 60C; each situated at an angle relative to the other linear portions. Preferably, the angles are different. The needle 60 preferably includes a leading portion 60A, an intermediate portion 60B and a trailing portion 60C.

The leading portion 60A of the needle 60 is sized to extend through the initial incision 400. The cross-sectional shape of the needle 60 is preferably substantially circular, but other cross sectional shapes such as, but not limited to, elliptical, polygonal, square and triangular are also contemplated herein. The diameter of the leading portion 60A is less than 5 mm, more preferably less than 4 mm, and even more preferably less than 3.5 mm to avoid damaging or displacing tissue. The sudden angle between the intermediate portion 60B of the needle and the leading portion 60A helps the surgeon avoid sudden lurches of the needle after the region 58 passes through the obturator fascia, as the intermediate 60B or trailing 60C portions of the needle can be grasped or abut external portions of the patient to stop an undesirable, sudden lurch through tissue. The angle also helps the surgeon steer the needle 60 along a desired or predetermined path.

The angle between the intermediate portion 60B and the trailing portion 60C is preferably greater than ninety degrees, more preferably, it is greater than one hundred and twenty degrees. The length of the trailing portion 60C should be sufficient to allow the surgeon to leverage the end of region 58 of the needle and drive it along its predetermined, desired path. This geometry helps direct the end of the region 58 back toward the surgeon. This geometry also helps the surgeon pass the needle through this portion of the body and emerge from the vagina without undue tissue trauma.

Figures 2, 3:
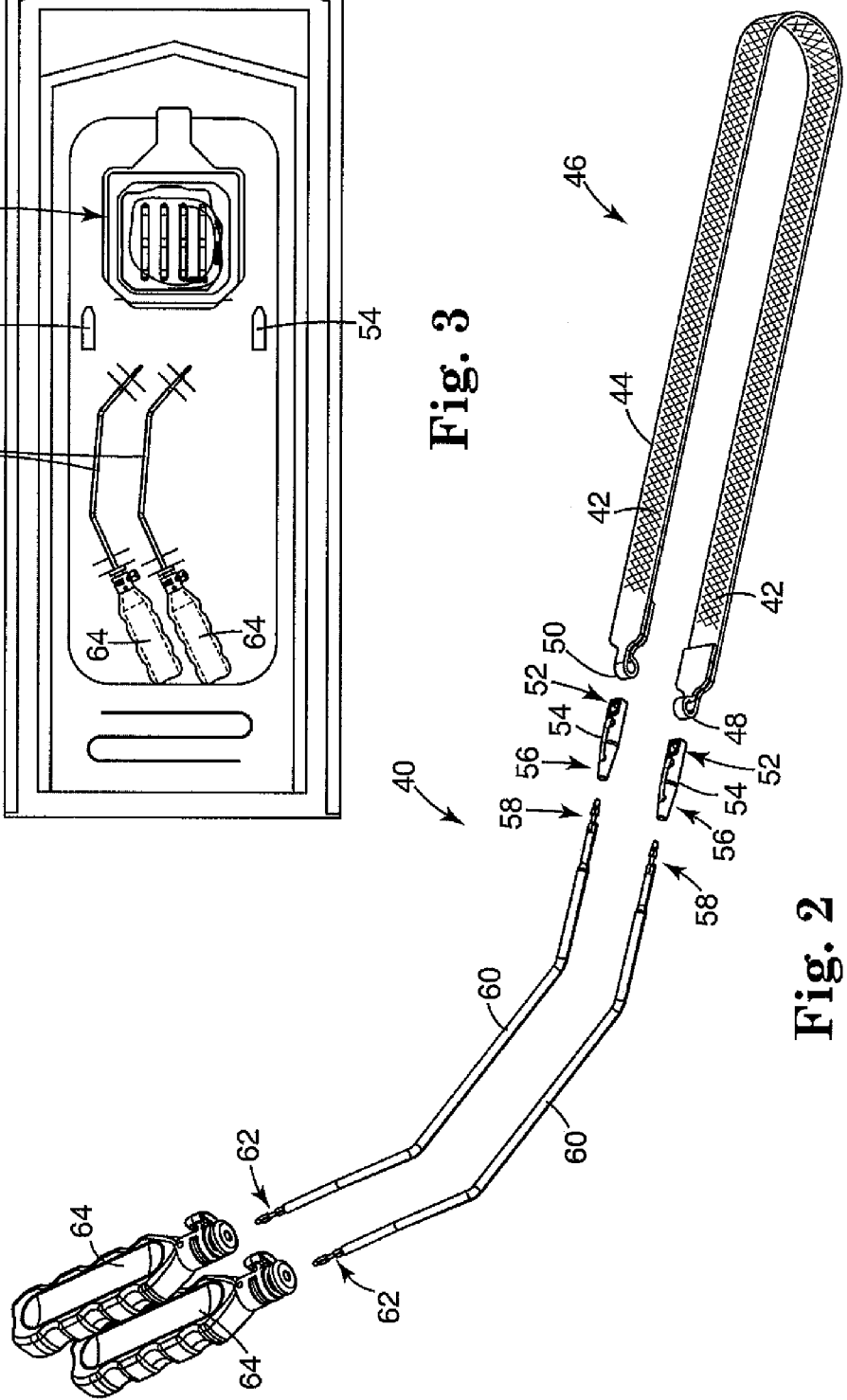
FIG. 2 is a perspective view of a needle, sling and additional optional elements for use in a kit according to an aspect of the present invention.
FIG. 3 is a top view of a kit according to one embodiment of the present invention.

FIG. 3 illustrates a kit 15 according to an aspect of the present invention. The kit 15 preferably comprises an implantable material (e.g. a sling mesh provided as part of a sling assembly 46), at least one (preferably two) optional handle 64, and at least one (preferably two) needle 60.

Figure 14:
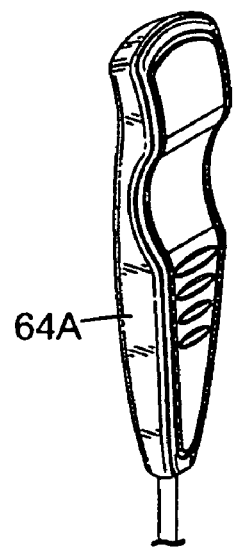
FIG. 14 is a perspective view of the handle of FIGS. 13A and 13B.
Figure 13A:
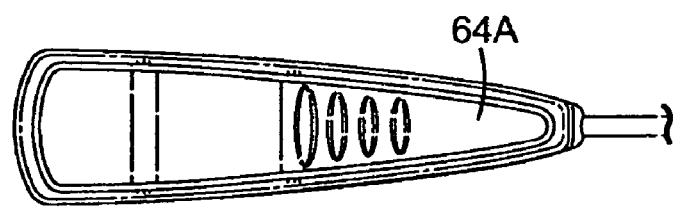
FIG. 13A is a front view of an optional handle suitable for use with the present invention.
Figure 13B:
FIG. 13B is a side view of the handle of FIG. 13A.
Figure 16:
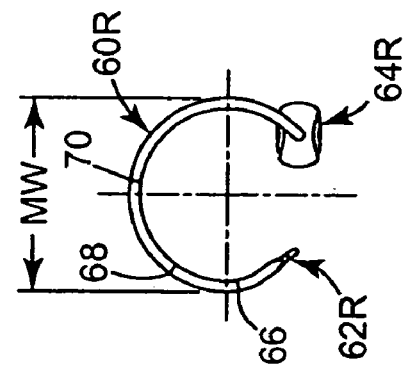
FIG. 16 is an end view of the needle of FIG. 15.
Figure 18:
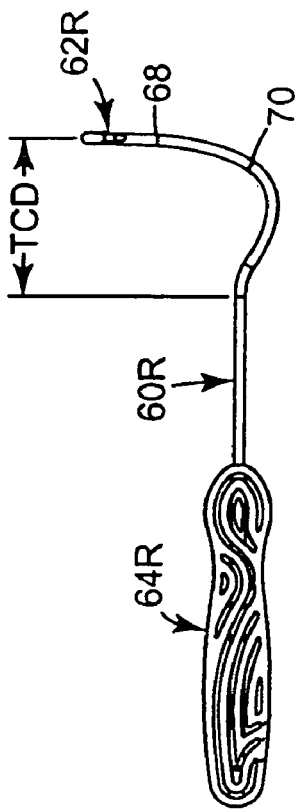
FIG. 18 is a bottom view of the needle of FIG. 15.
Figure 15:
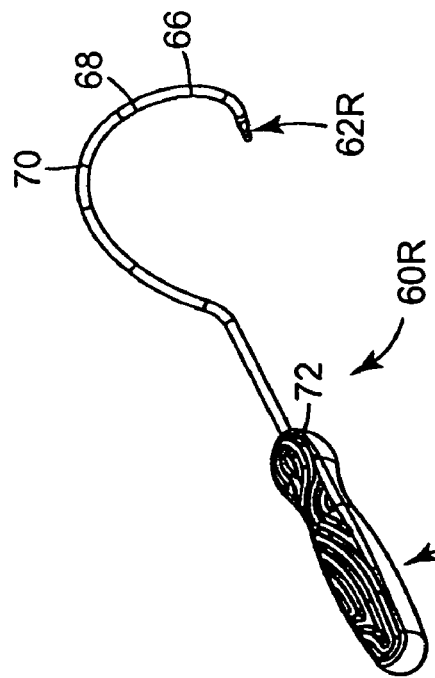
FIG. 15 is a perspective view of a surgical instrument particularly suitable for use on a right side of a patient's body, according to one aspect of the present invention.

The handle 64 is entirely optional. The handle may be removably attached to the needle, or it may be repositionably attached to the needle. Alternatively, the handle may be permanently attached to the needle 60. FIGS. 13 and 14 illustrate an optional shape of handle 64A suitable for permanent attachment to the needle 60. Other suitable handles are disclosed, for example, in U.S. Provisional Patent Application Nos. 60/347,494; 60/336,884 and 60/343,658.

The needle 60 is preferably made of a durable, biocompatable surgical instrument material such as, but not limited to, stainless steel (e.g. 316 stainless steel or 17-4 stainless steel), titanium, Nitinol, polymers, plastics and other materials, including combinations of materials. The needle 60 should have sufficient structural integrity to withstand the various forces (e.g. forces caused by dilator attachment, and penetration/passage of the needle 60 through the various tissues) without undergoing any significant structural deformation. Optionally, the needles 60 could be sufficiently malleable to allow a practitioner or user of the device to modify the needle 60 to a desired shape and, thereby, optimize the procedural approach.

Needles 60 may be disposable or reusable (e.g. sterilizable by steam sterilization procedures). In another aspect of the present invention, the needles 60 may be provided in a kit, such as any of the kits described in any of published U.S. Pat Application Nos. 2002-0151762-A1; 2002-0147382-A1; 2002-0107430-A1, US-2002-0099258-A1 and US-2002-0099259-A1; and U.S. Provisional Application Ser. Nos. 60/263,472, filed Jan. 23, 2001; 60/269,829, filed Feb. 20, 2001; 60/281,350, filed Apr. 4, 2001; 60/295,068, filed Jun. 1, 2001; 60/306,915, filed Jul. 20, 2001, and U.S. Provisional Patent Application No. 60/332,330, filed Nov. 20, 2001.

One embodiment of kit includes the needle 60 and other needles (not shown, but for example including the needles shown in published U.S. Pat. Application No. US-2002-0099258-A1) designed for placing a sling from the abdominal rectus fascia, under the urethra, and then back to the rectus fascia. If a traditional pubovaginal sling procedure seems to be an option for a patient but, during or prior to the surgical procedure, it becomes apparent that excessive scar tissue (e.g. due to a previous surgery) exists and would render the traditional procedure less desirable or impossible, then the needle 60 may be used in an alternative approach. Since the needles 60 are also provided in a kit, the surgeon has the option of conducting an alternative surgical procedure with the needles 60.

In another aspect of the present invention, a needle may optionally include the capacity to deliver a medicament (e.g. anesthesia) during the surgical procedure. For example, the needle 60 may be hollow with an open end. The needle may have a connector for associating with a medicament reservoir and delivery mechanism (e.g. a syringe).

The present invention may be utilized in conjunction with a wide variety of sling materials and sling assemblies. The sling may be integral, monolithic, or a composite of different components or segments of different components. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Suitable synthetic materials for a sling include polymerics, metals and plastics and any combination of such materials.

Commercial examples of non-absorbable materials include Marlex™(polypropylene) available from Bard of Covington, R.I., Prolene™ (polypropylene) and Mersilene (polyethylene terphthalate) Hernia Mesh available from Ethicon, of New Jersey, Gore-Tex™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon. Other examples of suitable materials include those disclosed in U.S. Pat. Application No. 2002/0072694. More specific examples of synthetic sling materials include, but are not limited to polypropylene, cellulose, polyvinyl, silicone, polytetrafluoroethylene, polygalactin, Silastic, carbon-fiber, polyethylene, nylon, polyester (e.g. dacron) PLLA and PGA. The sling material may be resorbable, absorbable or non-absorbable. Optionally, some portions may be absorbable and other portions may be non-absorbable.

The synthetic slings may be knitted, woven, sprayed or punched from a blank. Some slings may be sufficiently robust to be inserted without a protective sleeve. In other embodiments, some synthetic slings may have an associated protective sleeve (described in greater detail below) to assist with the implantation.

In one aspect of the invention, the sling may comprise a mesh material. The mesh material comprises one or more woven, knitted or inter-linked filaments or fibers that form multiple fiber junctions throughout the mesh. The fiber junctions may be formed via weaving, knitting, braiding, bonding, ultrasonic welding or other junction forming techniques, including combinations thereof. In addition, the size of the resultant openings or pores of the mesh may be sufficient to allow tissue in-growth and fixation within surrounding tissue. As an example, not intended to be limiting, the holes may comprise polygonal shaped holes with diagonals of 0.132 inches and 0.076 inches.

The quantity and type of fiber junctions, fiber weave, pattern, and material type influence various sling properties or characteristics. As another example, not intended to be limiting, the mesh may be woven polypropylene monofilament, knitted with a warp tricot. The stitch count may be 27.5 courses/inch (+ or −2 courses) and 13 wales/inch (+ or −2 wales). The thickness of this example is 0.024 inches. This embodiment of sling is preferably associated with a protective sleeve (described in greater detail below). Non-mesh sling configurations are also included within the scope of the invention.

Figure 29:
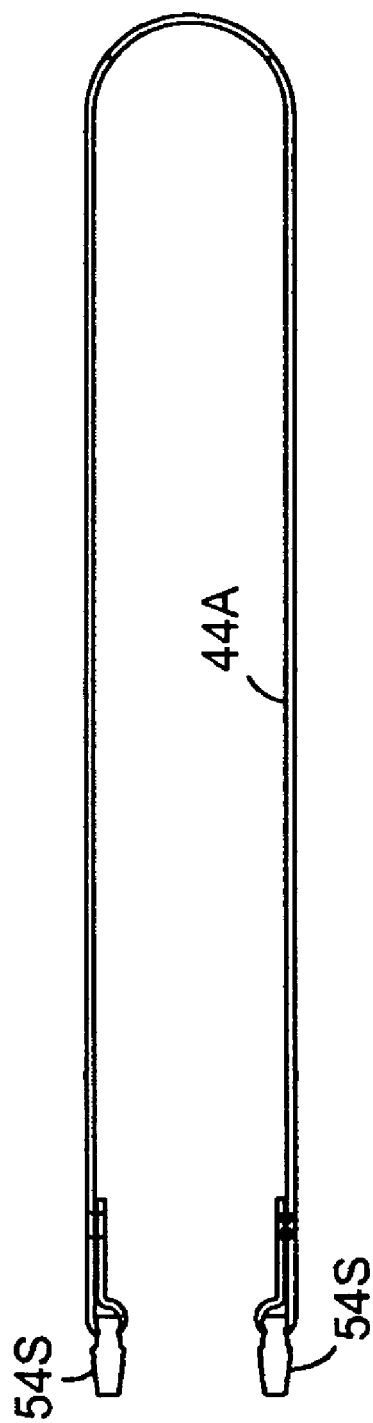
FIG. 29 is a side view of the sling assembly of FIG. 28.
Figure 30:
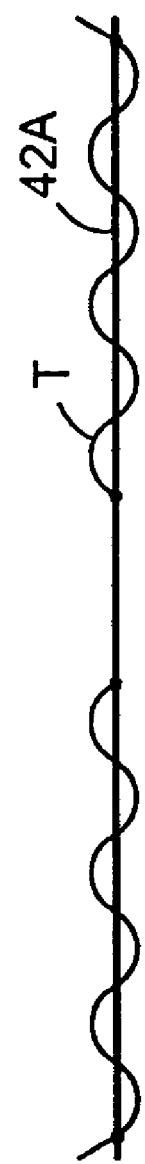
FIG. 30 is a side view of a sling and tensioning suture according to an aspect of the present invention.
Figure 31:
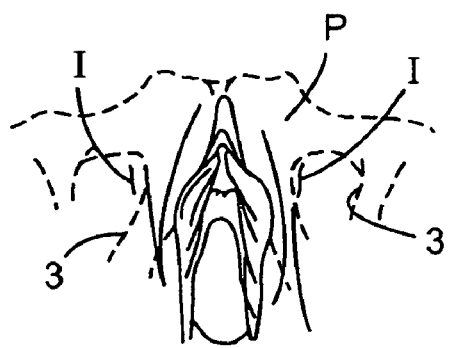
FIG. 31 is a schematic illustration of anatomical features, showing a pubic bone with dashed lines and incisions.

Referring to FIGS. 29 and 30, the sling mesh 42A is preferably elastic, as opposed to the substantially inelastic mesh available in Europe as Uratape® from Porges, and the tape described in Published U.S. Pat. Appl. No. 2002/0099260. As an example, a mesh may be tested to determine whether it is elastic using a series IX Automated Materials Testing System (an Instron), available from Instron Corporation. A 1 cm wide sample of the mesh may be placed in the Instron with a crosshead speed set at 5 in/min and a gauge length of 1 inch. An elastic mesh exhibits at least a 7% elongation under a ½ pound load, more preferably about a 10% elongation under a ½ pound load, and more preferably about 14% under the ½ pound load. An inelastic mesh exhibits less than an 7% elongation under a ½ pound load.

The mid-portion of the sling mesh (the portion designed to reside underneath the midurethra) is preferably substantially free of any silicone coatings. In yet another embodiment (e.g. shown in FIG. 28), the mid-portion of the sling may comprise a non-synthetic material, constructed according to the teachings of U.S. Provisional Patent Appl. No. 60/405,139, filed Aug. 22, 2002; Other suitable synthetic slings are described in published U.S. Pat. No. 2002-0138025-A1, published Sep. 26, 2002.

In another embodiment the sling material may have one or more substances associated therewith through a process such as coating or they may be incorporated into the raw material of the sling. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, reduce the chances of tissue erosion, enhance visualization, indicate proper sling orientation, resist infection or other effects.

While the slings are preferably rectangular for treating SUI in females, other shapes are also contemplated. Depending on the treatment addressed (e.g. to provide hammock support for the bladder or bladder neck, or to address a rectocele, enterocele or prolapse) the slings may be any of a wide variety of shapes. As an example, the sling may be of the general shape of the slings described and shown in Moir et al., *The Gauze-Hammock Operation*, Journal of Obstetrics and Gynaecology of the British Commonwealth, Volume 75, No. 1, Pps. 1-9 (1968).

Figure 12:
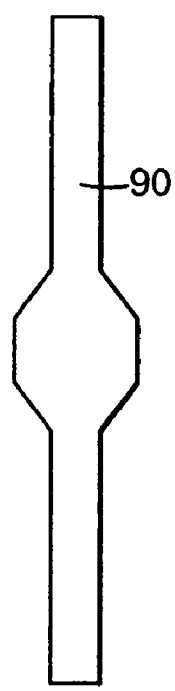
FIG. 12 is a top view of another embodiment of sling for use in accordance with the present invention.

FIG. 12 shows a sling 90 with a shape other than a purely rectangular shape. This embodiment of sling 90 includes a mid portion that is wider than the remaining portions of the sling 90. The mid portion is preferably placed under the urethra 16, along the mid portion of the urethra.

FIG. 2 illustrates a sling assembly 46 comprising sling 42 and sheath 44. Preferably, the overall dimensions of the sling assembly 46, including insertion sheath 44 and sling 42 are sufficient to extend from a superficial incision 400 near the obturator fascia (see FIGS. 4 through 8), to an undersurface of the urethra 16 and back to another incision 400 in obturator fascia that is opposite the first incision. The size of the sling can take into account the imprecision associated with the range of human anatomy sizes. In a preferred embodiment, the sheath length of the assembly of the present invention is approximately within the range of 10 cm to 50 cm, sheath width is approximately within the range of 1.0 cm to 2 cm, and sheath material thickness is approximately within the range of 0.127 mm to 0.203 mm, respectively. The associated sling 42 has a length, width and thickness approximately within the range of 7 cm to 50 cm; 1.0 cm to 2 cm; and 0.508 mm to 0.711 mm, respectively.

The sling 42 of the present invention can be implanted without the need for bone screws. The precise, final location of the sling 42 will depend on a variety of factors including the particular surgical procedure(s) performed, and any preconditions of the patient such as scar tissue or previous surgeries. For example, it may be preferred to place the sling 42 in close proximity to, but not in contact with, a mid portion of the urethra to treat incontinence. Alternatively, the sling may be placed near the bladder neck.

Preferably, the sling 42 has a tensioning filament or suture T as disclosed, for example, in U.S. Published Pat. Application No US-2002-0107430-A1. The tensioning suture T may be constructed from a permanent or absorbable material. Also preferably, the sling 42 comprises a substantially elastic, polypropylene sling such as a sling constructed from the polypropylene sling material available in the SPARC Sling-System, available from American Medical Systems of Minnetonka, Minn.

FIG. 30 illustrates an embodiment with the tensioning filament T extending along end portions, but not extending along a mid-portion of the sling. The sling 42A comprises a polypropylene sling mesh 42A. It is constructed of polypropylene monofilament that is precut to about 1.1 cm width×35 cm length. The tensioning filaments T in this embodiment are fixed at each end to the sling material (e.g. a polypropylene mesh) by welding (e.g. ultrasonic), knotting, anchoring, adhering (e.g. with and adhesive) or the like. Absorbable tensioning sutures T are threaded into the length of the sling mesh 42A from each end to allow for tensioning adjustment of the sling mesh 42A after placement in the patient is achieved. The mid portion of the sling mesh 42A is preferably free of the tensioning sutures T. For example, approximately 5 mm may separate the ends of the two tensioning sutures T.

Two plastic sheaths 44A (see FIG. 29) that overlap in the center of the sling mesh cover the sling mesh and protect it during placement. The plastic covering over the mesh is designed to minimize the risk of contamination.

Referring to FIG. 2, a protective sheath 44 is preferred, especially when the sling 42 is elastic. A sheath is particularly desirable when the sling is elastic as the sheath 44 assists in introduction of the sling within tissue and avoids damage to the elastic sling material. The sheath 44 is used during insertion of a synthetic sling 42. After the sling 42 is implanted, the sheath 44 is removed and discarded. Preferably, the protective sheath 44 is constructed of a material that affords visual examination of the implantable sling material 42 and that affords convenient passage of the assembly 46 through tissue of the patient.

In a preferred embodiment, the sheath 44 is made of polyethylene. Other materials including, without limitation, polypropylene, nylon, polyester or Teflon may also be used to construct the sheath 44. The sheath 44 should also conveniently separate from the sling material 42 after the sling 42 is implanted without materially changing the position of the sling 42.

The sheath 44 may comprise two elongate, separable sections. Optionally, portions of the sheath 44 may detachably and telescopically overlap near the middle portion of the sling or it may be slit (e.g. longitudinally or perpendicular to the longitudinal axis) to afford convenient separation.

In another aspect, the present invention comprises a dilator 54 (FIG. 2) for use in a surgical sling procedure. Notably, the dilator is optional according to some aspects of the present invention as, for example, the sling and/or protective sheath may be directly connected to a novel needle of the present invention by virtue of an eyelet in the needle or other arrangements disclosed in greater detail below.

The dilator 54 comprises a body portion having first end portion 56 and second end portion 52 opposite the first end portion 56. The first end portion 56 has surfaces for associating the dilator with a needle (e.g. region 58 of needle 60). The second end portion 52 has sling association means for associating the article with a sling, sling assembly or component thereof. The sling association means may comprise a hole 90.

Preferably, the dilator 54 comprises a short article that dilates a needle track for ease of sling introduction and positioning within the patient. Region 58 of the needle 60 is preferably keyed to allow for convenient, secure attachment of the needle 60 relative to the dilator 54. Preferably the attachment is permanent.

The kit shown in FIG. 3 includes two dilators 54. The dilators 54 atraumatically create and/or expand the passageway through the tissues for sling assembly delivery. The dilator 54 is preferably short relative to a needle 60 for ease of passage of the assembly and to reduce the overall amount of tissue that is deflected at one time. Preferably, the dilator is less than 2.5 inches in length, and more preferably, it is less than one inch in length, even more preferably, it is less than 0.7 inches in length. The maximum radius of a dilator 54 is preferably less than 10 mm, more preferably less than 7.5 mm, even more preferably less than about 5 mm. The tip or leading end of the dilator 54 is preferably blunt, as, in preferred embodiments, the leading tip of the dilator 54 will pass through tissue that has already been pierced by a needle 60. The dilator 54 may be made from a variety of biocompatible and sterilizable materials including, without limitation, acetal, polycarbonate, polypropylene, Delrin®, Acrylonitrile-Butadiene-Styrene (ABS), polyethylene, nylon and any combination of biocompatible materials.

The dilator 54 preferably includes means for associating with a surgical needle 60. In a preferred embodiment, the association means affords a permanent affixation between the dilator 54 and the needle 60. By "permanent affixation", it is meant that it would be very difficult to manually separate the dilator from the needle after they have become permanently affixed. After implantation of the sling 42, to separate the sling 42 from the dilator 54/needle 60, the surgeon cuts an end of the sling 42 as described more fully below. The association means preferably affords quick and convenient attachment of the dilator 54 to the needle 60 to avoid wasting time in the midst of a surgical procedure. The attachment should also be secure to avoid separation of the needle 60 and dilator 54 while the combination is passed through tissue.

In one embodiment, the means comprises a shoulder surface on the needle and complementary slot surfaces on the dilator 54. Referring to the embodiment of dilator shown in FIG. 2, the dilator 54 may be approximately 3.1 cm (1.2 inches) in length. The dilator 54 preferably includes a gentle taper near its first end 56. The dilator is sized and shaped to provide atraumatic passage through body tissue. The taper and relatively smooth outer surface of the dilator 54 facilitate atraumatic passage of the dilator 54 and attached sling assembly 46 through the various tissues of the patient. The presence of the dilator 54 allows a gentle transition between the diameter of the needle, to the shape of the dilator, and finally to the sling assembly 46.

Preferably, the attachment of the dilator 54 to the needle 60 is a substantially linear fashion, as opposed to a twisting or screw-like attachment. Preferably, the attachment is a snap-fit attachment to save time during the surgical procedure.

The second end 52 of the dilator 54 associates the dilator with one end of a sling 42, or sheath 44 or sling assembly 46. The sheath 44 or sling 42 is preferably attached to the dilator 54 via a first opening or through-hole located near the second end 52 of the dilator 54. In this embodiment, the opening operates as a universal sling material or assembly attachment point which can receive a variety of materials, such as fascia, autologous materials, synthetics, biologic tissues and any other similar tissues, including any combinations.

In the embodiment shown in FIG. 2, the end portion 48 or 50 of one end of the sheath 44 is threaded through the opening of the dilator 54 and secured to the sheath 44, thereby forming a loop. Alternatively, ends 48 or 50 may be fastened onto the sheath 44 via ultrasonic welding, bonding, melting, suturing, sealing or other attachment techniques. Further, the end 52 of the dilator 54 preferably includes a cut-away section to provide room to receive sling assembly material to reduce the overall profile of the sling assembly experienced by tissue during sling passage. Therefore, when the sheath is attached to the cut-away section, the additional sheath material is not apt to significantly increase the relative thickness, diameter or profile of the dilator 54. Unlike the showing in FIG. 3, the dilator 54 is preferably preattached to the sling assembly 46. In one embodiment, the sling 42 itself may be attached to the dilator, e.g. with a suture threaded through the opening of the dilator and tied to the sling.

One or more longitudinal slots located on the outer surface of the dilator 54 allow the wall of the dilator 54 to expand in a radially outward direction when the first end of the needle 60 is inserted into the opening of the dilator 54. When a shoulder of the dilator 54 passes the recess of the needle 60, the wall of the dilator 54 collapses around the needle 60 as the shoulder seats into the recess, thereby securing the dilator 54 on the needle 60 and blocking separation of the dilator 54 and needle 60.

A portion of the dilator 54 includes a taper having a decreasing profile toward the second end 56 of the dilator 54. The taper preferably gently cams tissue out of the path of the sling assembly 46 as the sling assembly is inserted in the body. The taper is also sized and shaped to reduce the amount of friction or resistance as the device is drawn through the tissues of the patient. The amount of force required to manipulate the device through the tissues is thereby reduced. This in turn provides the user of the assembly with additional control over device insertion and maneuverability through tissue and within the patient. In addition to tapered profiles, other dilator profiles such as conical, flared, frusto-conical, pyramid-shaped, elliptical or other applicable profiles may also be used.

A surgical kit according to the present invention may optionally include additional accessories. For example, a surgical drape specifically designed for urological procedures such as a sling procedure may be included in a kit of the present invention. Such a drape is disclosed in published U.S. Pat. Appl. No. 2002-078964-A1. Alternatively, an article for objectively setting tension of the sling, such as one of the articles described in U.S. patent application Ser. No. 09/968, 239, filed Oct. 1, 2001 may be included in the kit.

The kits according to the present invention preferably include at least two needles. In some instances the needles may be substantially identical, in other instances, they may be different. Two or more needles reduce the need to reuse a non-sterile needle at a different location with a patient, thereby eliminating cross contamination issues. Additional needles, handles, dilators and other elements may also be included for surgical convenience, for avoidance of contamination from one portion of the body to another, for ease of manufacturing or sterilization or for surgical requirements. For example, two different types of needles may be included in a kit. One type of needle may be suitable for an outside-in (e.g. from the skin incision toward a vaginal incision) approach. Another type may be suitable for an inside-out (e.g. from the vaginal incision toward a skin incision) approach. Surgeons that prefer an approach dictated by the surgeon's dominant hand may prefer this embodiment. Alternatively, a universal needle (e.g. one suitable for both an inside out and an outside in approach) may be utilized.

Figure 53:
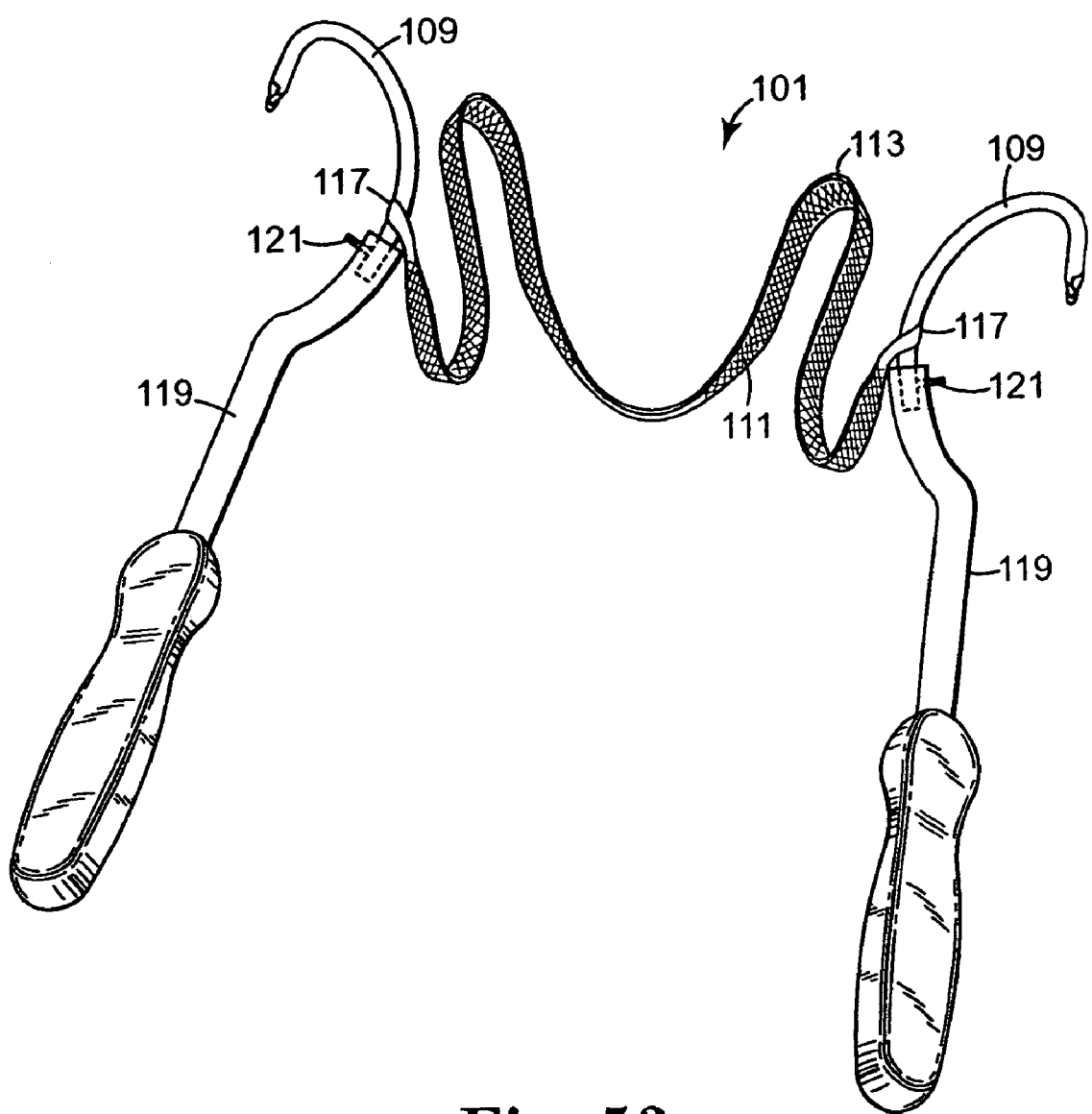
FIG. 53 is a perspective view of a system for use in an inside out procedure according to the present invention that includes a portion that is at least partially reusable.

FIG. 53 illustrates a system 101 for use in an inside-out procedure. The system 101 comprises a pair of needles 109 that are sized and shaped for the inside-out approach. The system 101 also includes a sling assembly comprising a sling 111, and protective sheath 113. The sling assembly may be permanently attached to the needles 109 at regions 117. Alternatively, the needle 109 can include specially shaped structure (e.g. an eyelet) in region 117 that affords association between the needle 109 and sling or sling assembly after passage of the needle 109. The system 101 may optionally include releasable handle portions 119 that can be releasably attached to the needles 109 at ends 121.

Figure 54:
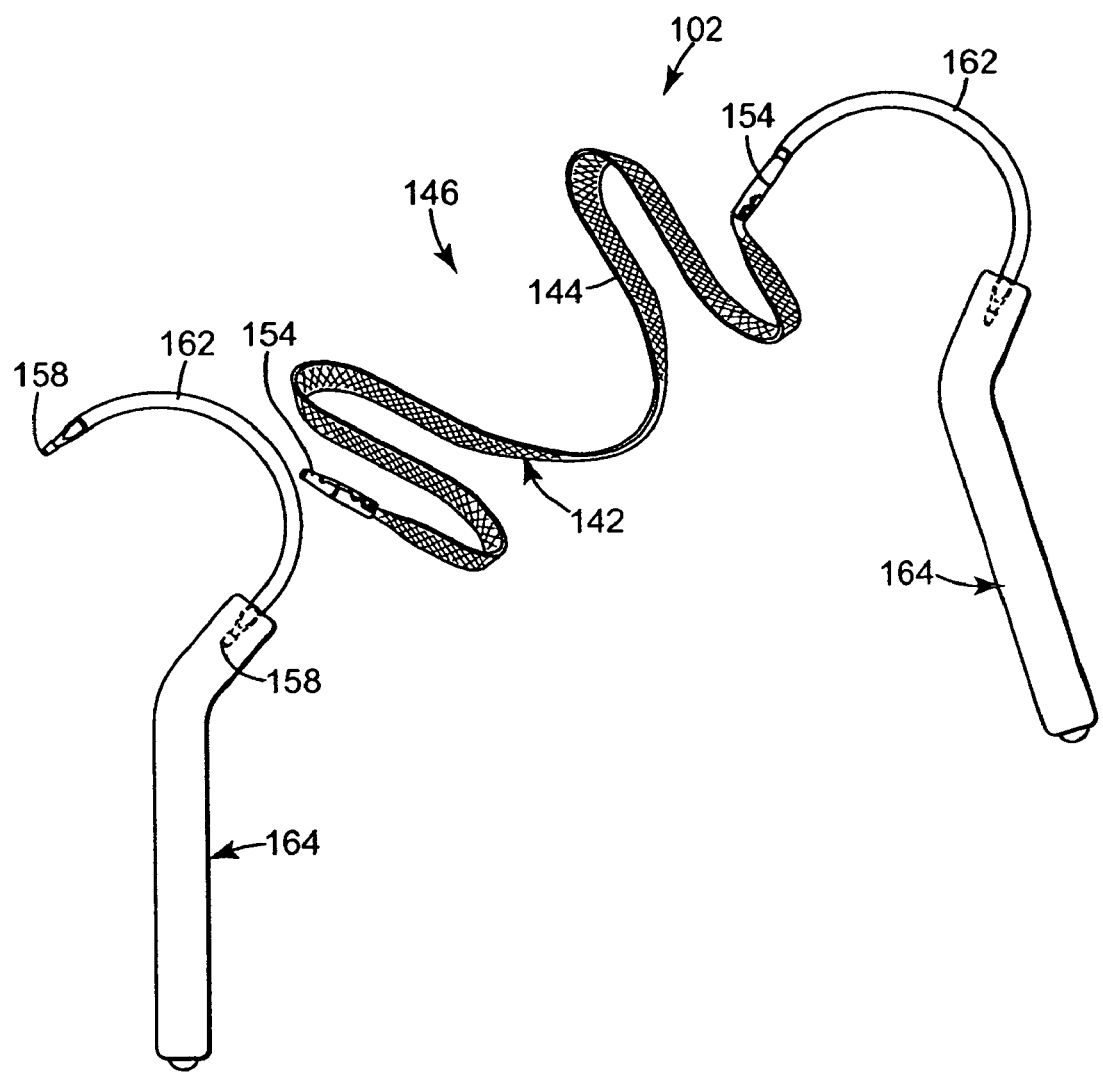
FIG. 54 is a perspective view of a universal system capable of use in inside-out and outside in approaches according to the present invention, which system includes a needle having two regions capable of attachment to either a handle or a sling assembly.

FIG. 54 illustrates a system 102 for use in either an inside-out procedure or an outside-in procedure. The system 102 comprises a sling assembly 146 having a sling material 142, a sheath 144 and dilators 154. The system includes a handle portion 164 that is at least partially reusable. Needles 162 are suitable for either an inside-out or outside in procedure. The regions 158 of the needles 162 may be attachable to either a dilator 154 or the handle portion 164. Alternatively, the needles may be attachable to the implantable material itself or a sling and protective sleeve assembly without any dilator.

The system 102 allows the needles to be passed through tissue without requiring that they be attached to a sling or sling assembly. Thus, if the initial passage is not deemed to be optimum, the needles may be repassed without subjecting the sling or sling assembly to damage during the-initial passage.

Figure 55:
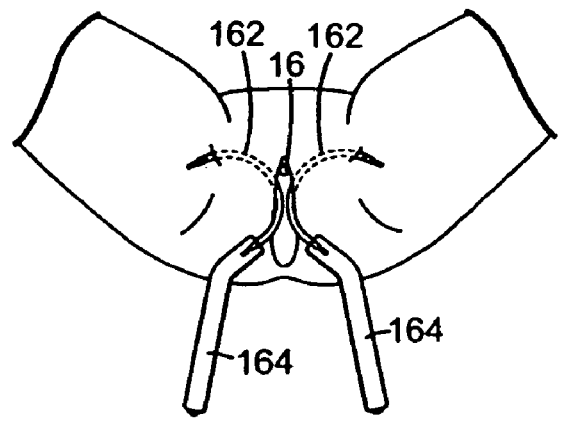
Figure 56:
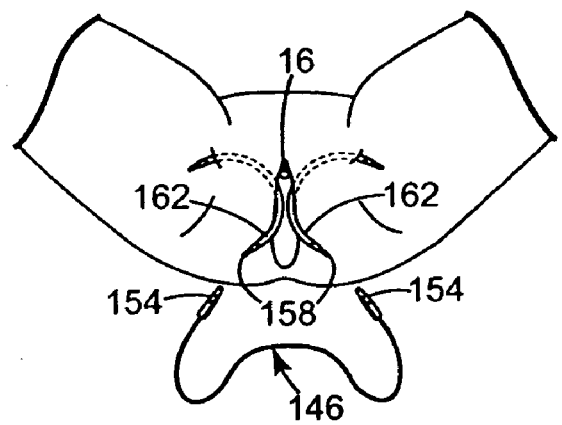
Figure 57:
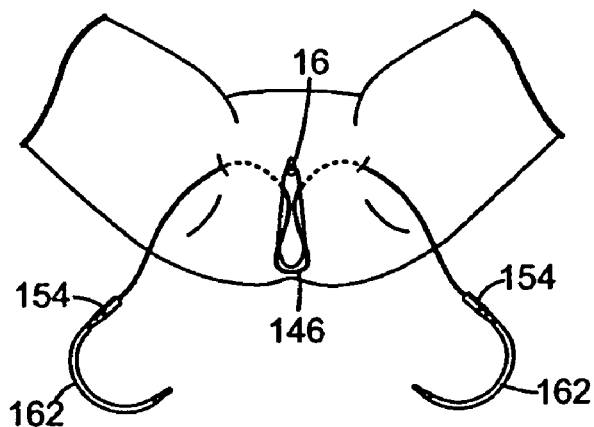

FIGS. 55-57 sequentially illustrate use of the system 102 using an inside-out approach. FIG. 55 illustrates passage of the needles 162 using inside-out approaches. The handles 164 are optional. If they are used, they are removed once the needles 162 have emerged from the skin incision. FIG. 56 illustrates the needles 162 after the handles 164 have been removed, in preparation for attachment of a sling assembly 146 on the regions 158 of the needles 162 previously occupied by the handles 164. FIG. 57 illustrates the system 102 during implantation of the sling.

Figure 58:
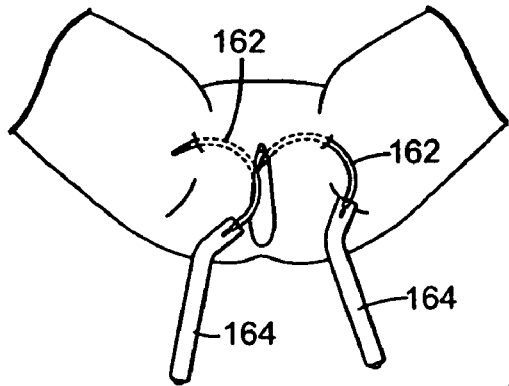
FIG. 58 is a schematic illustration of the system of FIG. 54 used in an inside-out approach (the right side of the patient) and an outside-in (the left side of the patient) approach.

FIG. 58 is a schematic illustration of the system 102 used in an inside-out approach (the right side of the patient) and an outside-in (the left side of the patient) approach. This combination may be utilized, by a right-handed surgeon who prefers to pass the leading edge of the needle with his or her dominant hand. Alternatively, the combination may be reversed for a left-handed surgeon. The remainder of the surgical procedure may be substantially identical to that depicted in FIGS. 56 and 57. Notably, the handle 164 utilized on the right side of the patient's body may optionally be placed on the other side of the needle after it emerges from the patient's body to conveniently assist the surgeon in moving the needle 162 and sling assembly 146 through the tissue.

Figure 59:
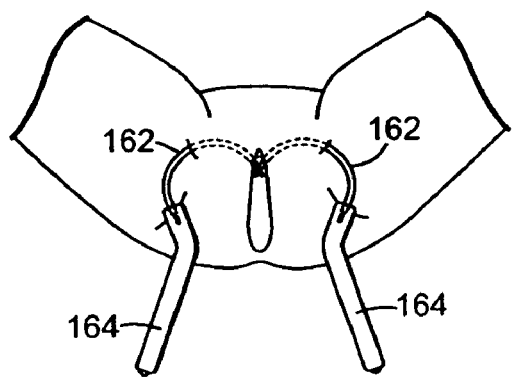
Figure 60:
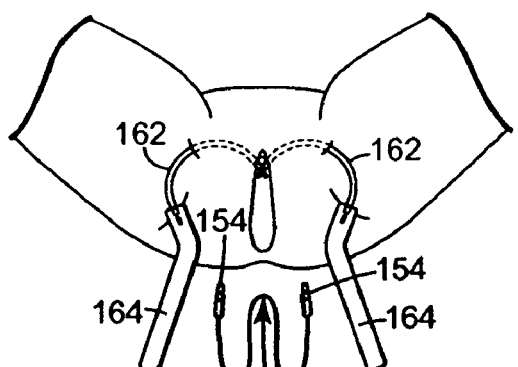
Figure 61:
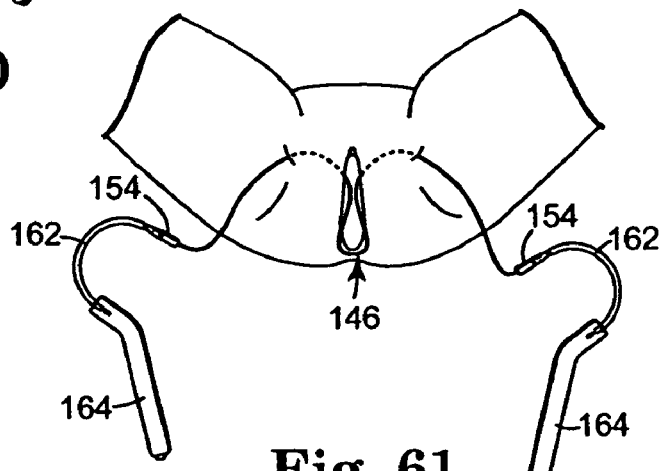

FIGS. 59-61 sequentially illustrate the system 102 used in outside-in approaches. FIG. 59 illustrates the needles 162 inserted initially through the patient's skin and thereafter emerging from a vaginal incision. FIG. 60 illustrates the system 102 just prior to attachment of a sling assembly 146. FIG. 61 illustrates the system 102 during implantation of the sling.

Figure 62:
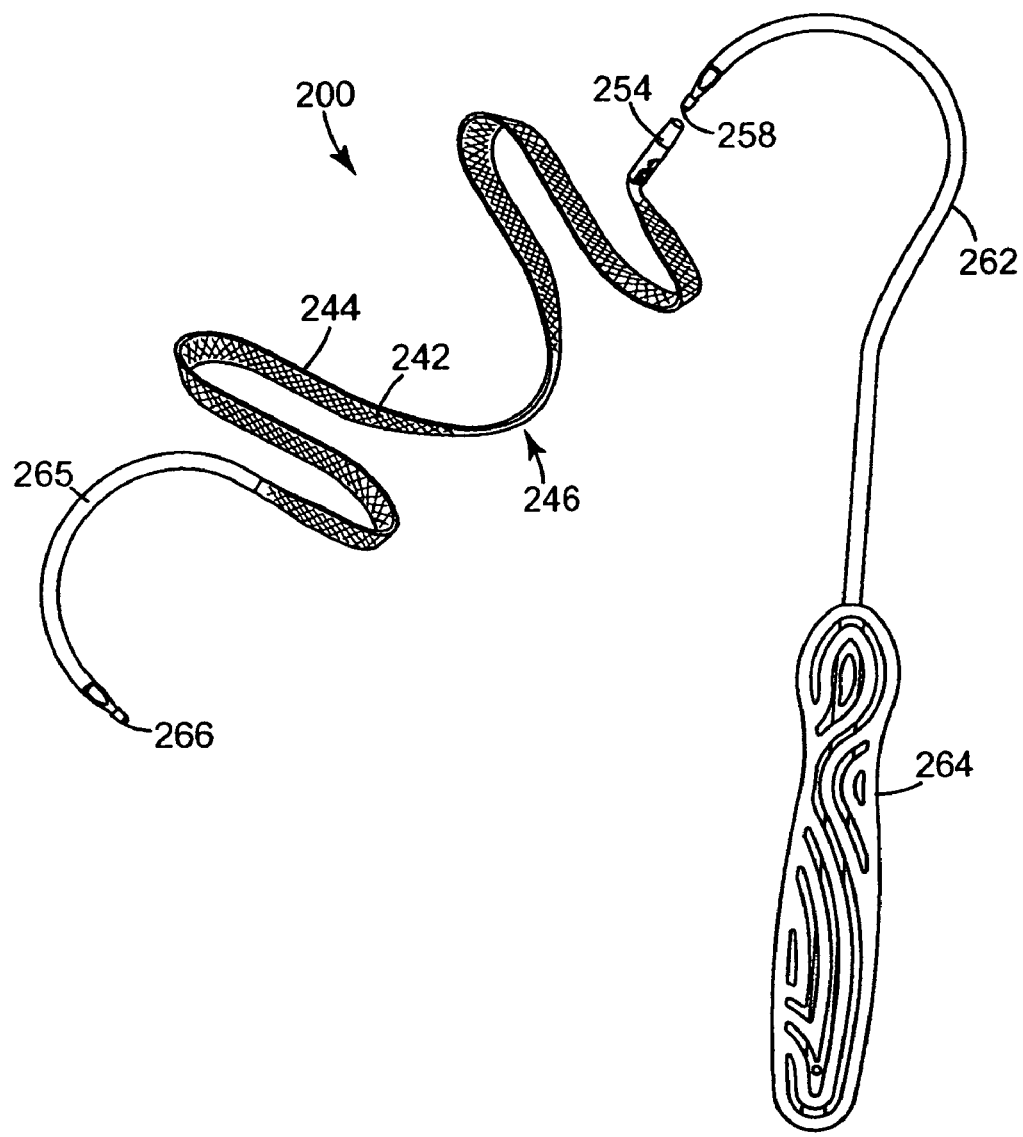
FIG. 62 is a perspective view of another embodiment of surgical assembly according to the present invention, with a needle suitable for an outside-in approach (e.g. on the left side of the patient's body) and a sling assembly with a needle attached thereto suitable for an inside-out approach (e.g. through the right side of the patient's body)

Referring to FIG. 62, there is shown another system 200 according to the present invention. The system 200 comprises a needle 262 suitable for an outside-in approach on the left side of the patient's body and associated handle 264. The system 200 also includes a sling assembly 246 comprising a sling 242, protective sheath 244 and dilator 254 at one region. The dilator 254 is designed to mate with the region 258 of the needle 262. At the other end of the sling assembly 246, a needle 265 may be permanently attached to the sling assembly 246. The needle 265 is sized and shaped to be suitable for an inside-out approach on the right side of a patient's body. The needle 265 includes a leading region 266 suitable for that purpose. The leading region 206 may include a portion that is blunt or, alternatively somewhat sharpened. The system 200 is particularly suitable for a surgeon that desires to initially pass needles with his or her dominant hand. The depicted system 200 is suitable for a right-handed surgeon. A mirror image or reverse system is particularly suitable for a left-handed surgeon that desires to initially pass a needle with his or her left hand.

Optionally, the system 200 could include a detachable handle for the needle 265 to assist in passage of the needle 265. Also optionally, the needle 264 may be omitted from the system. Instead, the needle 265 may be used to pass the sling initially using an outside-in approach on one side of the body and then continuing to insert the sling using an inside out approach on the other side of the body.

Figure 28:
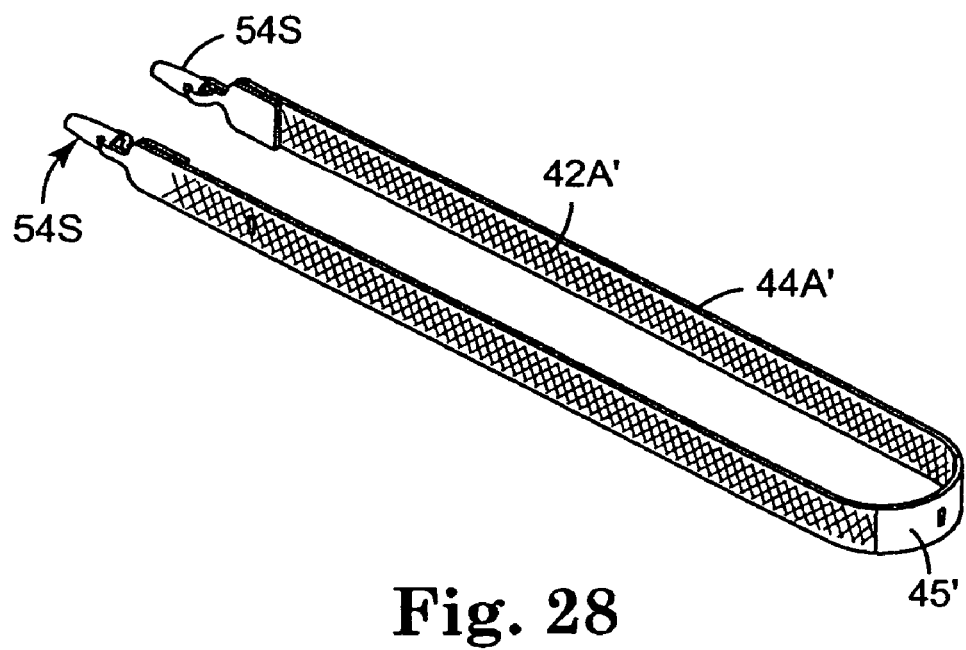
FIG. 28 is a perspective view of one embodiment of a sling assembly according to the present invention.

In a preferred embodiment, a kit comprises two surgical instruments such as those shown in FIGS. 15-22, and a polypropylene sling mesh assembly with attached dilators as shown in FIG. 28. Such a kit may be provided for the placement of a pubourethral sling for the treatment of female stress urinary incontinence (SUI) resulting from urethral hypermobility and/or intrinsic sphincter deficiency.

Figure 23:
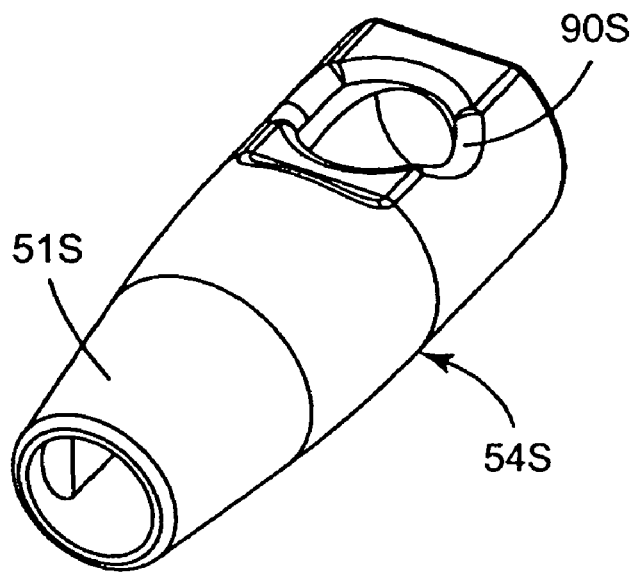
FIG. 23 is a perspective view of a short dilator for use in accordance with an aspect of the present invention.
Figure 23A:
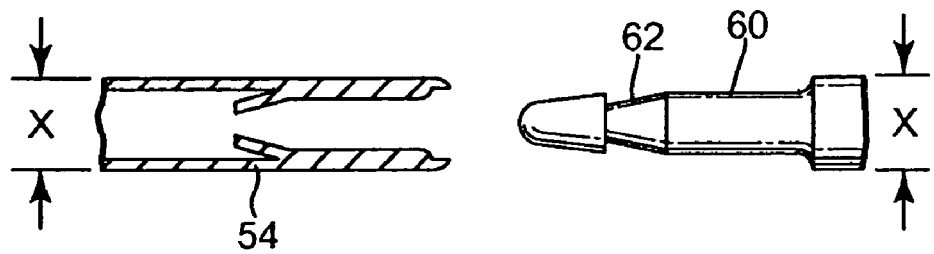
FIG. 23A is a sectional view of another embodiment of dilator in proximity with another embodiment of a needle.
Figure 23B:
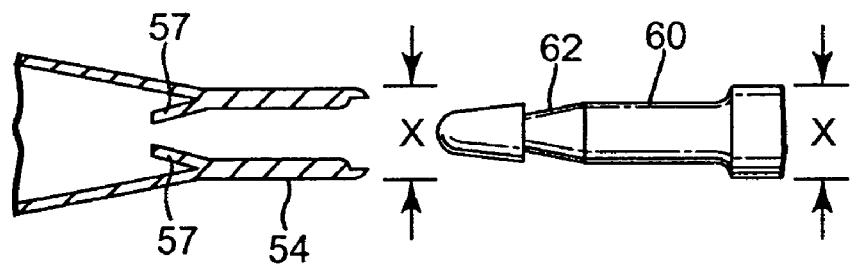
FIG. 23B is a sectional view of another version of a dilator and the needle of FIG. 23A.
Figure 23C:
FIG. 23C is a sectional view of another embodiment of a dilator and needle combination.
Figure 25:
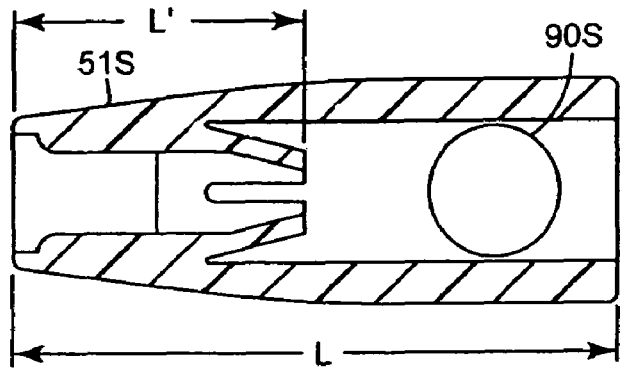
FIG. 25 is sectional view of the dilator of FIG. 23 in accordance with an aspect of the present invention.
Figure 25A:
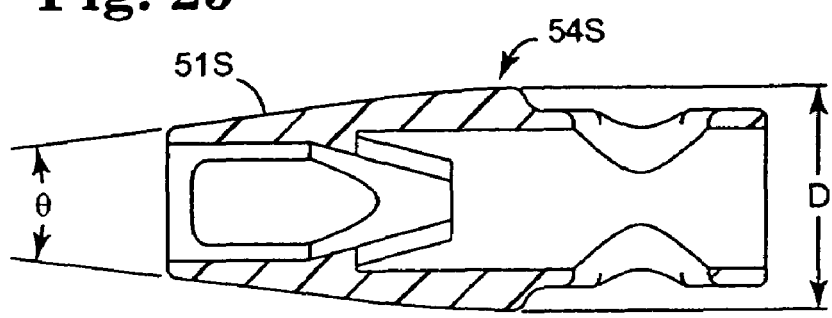
FIGS. 25A and 26 are another sectional view of the dilator of FIG. 23 illustrating different features.

In a further preferred embodiment, a dilator used for associating the sling with the surgical instrument is shown in FIG. 23A. Dilator 54 is shown having a diameter X that is substantially the same as the diameter x of the needle 60. By making the diameter of the dilator the substantially the same size as that of the needle, the system can avoid subjecting tissue to a sudden discontinuity as it moves through tissue. This low profile can assist in effectively and efficiently implanting the sling material. In FIG. 23B, the dilator is shown having a diameter that matches the diameter of the needle at one end thereof, and gets larger towards the other end. In FIG. 23C, another low profile dialator and needle combination is shown. In this further low profile embodiment, any flats on the needle and on the mating surfaces within the connector have been removed. The removal of any flats allows the needle and connector to be quickly and easily connected without worrying about proper orientation of the connector relative to the needle. This embodiment also allows the connector to rotate during passage within the body and thus may decrease the resistance of the passage of the needle once the connector has been attached to the needle end. In addition, the needle end is recessed and the connector's leading edge may be hidden in this recess rather than extending beyond the diameter of the needle. This embodiment avoids any exposed edge or lip at the interface of the connector and needle. The smaller profile further provides less dilation by the connector during withdrawal and reduces the resistance to withdrawal of the needle once the connector has been attached. Still further, the smaller connector creates a smaller opening the body during passage which may aid in the anchoring of the sling into the area of deployment. The smaller channel that the sling is placed in may provide greater anchoring forces on the sling immediately after deployment and before ingrowth. Finally the overall amount of the connector that extends beyond the tip of the needle and the overall length of the connector is shortened in this embodiment. Because the connector is relatively straight, any amount that the connector extends beyond the tip of the needle may actually increase the resistance during withdrawal and may actually result in more trauma and dilation to the tissue than may be desired.

The individual elements of the kits of the present invention may be packaged together, separately or in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), gamma or plasma procedures. For example, the surgical instrument may be reusable or single use devices.

Figure 11:
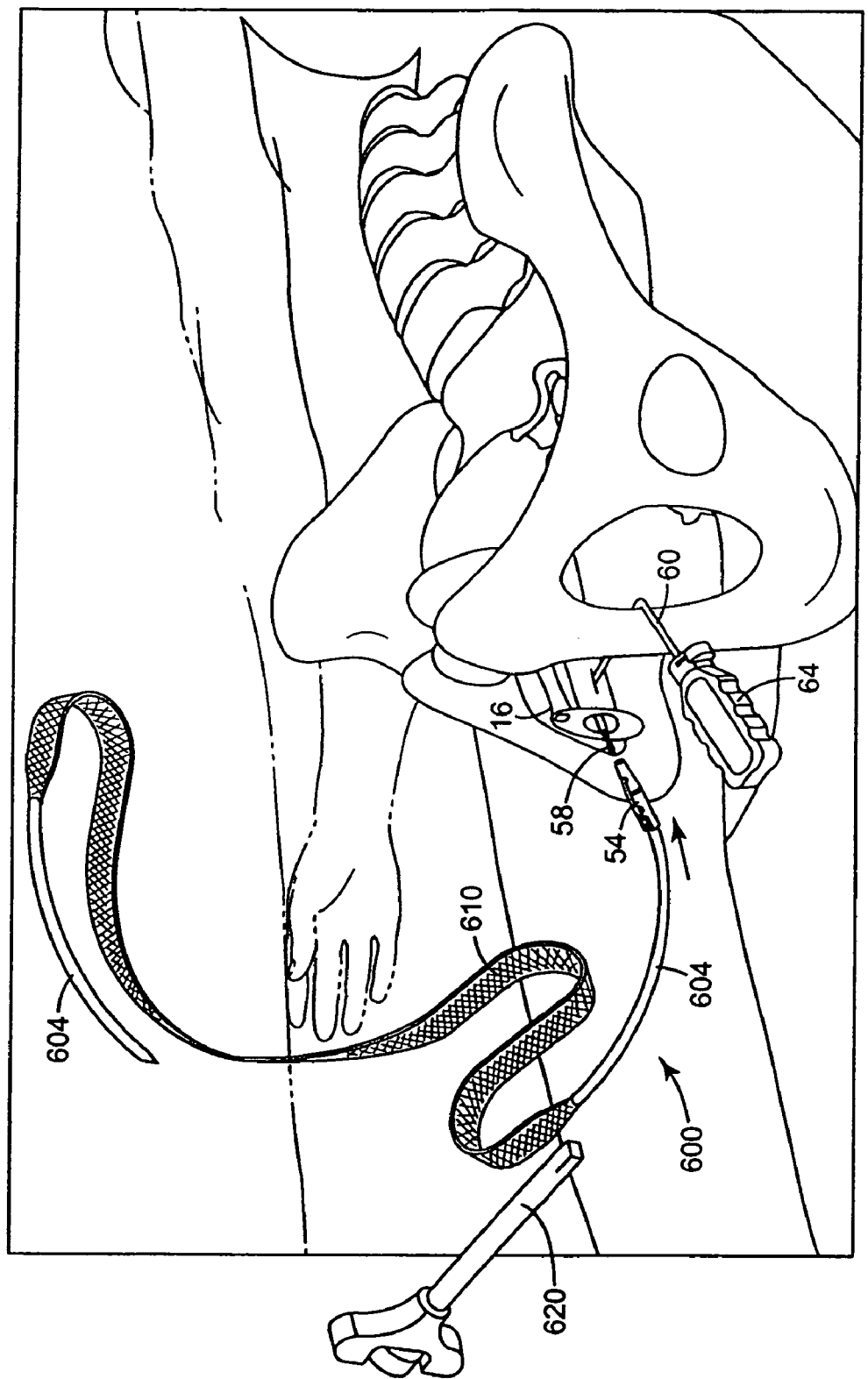
FIG. 11 is a schematic view of another embodiment of the present invention.

FIG. 11 shows another embodiment of the present invention. The Figure is schematic and is not to scale. Some features are exaggerated or omitted to illustrate or emphasize other details. For example, the vaginal incision is only shown schematically and should not be interpreted as identifying a preferred size, shape or location of the incision.

In this embodiment, the needle 60 acts as a surgical guide needle (e.g. with a diameter of about 4 mm, or less, preferably about 3 mm) for a relatively larger sling transport needle 604 (e.g. with a diameter of about 5 mm or less). Preferably, the sling transport member has a sling assembly 610 (e.g. a sling mesh and insertion sheath) attached thereto. Alternatively, the sling transport needle 604 may have a more exaggerated hook shape, similar to the shape shown in PCT WO 02/39890.

The guide needle 60 serves a different purpose than the surgical transport needle 604. The surgical guide needle 60 is preferably small and has a blunt tip. The blunt tip is initially inserted through incision 400 adjacent obturator fascia and then through a vaginal incision. Inserting a small, blunt needle in this fashion provides the surgeon with additional control in maneuvering through the anatomy of a patent and in avoiding sensitive tissue.

A surgical kit according to an aspect of the present invention may include a dilator 54 for placement on a tip of needle 60. The sling transport needle 604 may optionally include a sharp tip. The dilator 54 receives the tip of the needle 604. A technique of pushing sideways on the sling transport needle 604 with one hand while steering the tip of the needle 604 by holding guide needle 60 with the other hand may be used to implant the sling.

Alternatively, the dilator 54 may include surfaces for firmly engaging and attaching to needle 604. Those surfaces can include mechanical interlocking structures, grasping structures or interlocking structures. As a result, the needle 60 need not have specially shaped surfaces 58 for engaging the dilator and can instead have cylindrical surfaces adapted to be received within the dilator.

Figure 27:
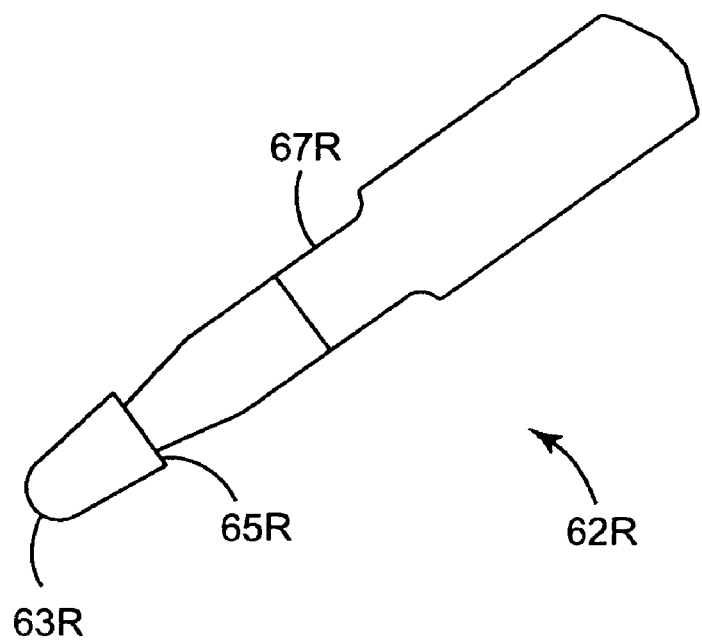
FIG. 27 is a side view of a distal region of a needle according to the present invention; showing a specially designed shape that is complementary to inner surfaces of the dilator of FIG. 23.

Referring to FIGS. 15, 16, 17 and 18, there is shown a novel needle 60R according to the present invention. The needle 60R is particularly suitable for passage on the right side of a patient's body, initially from an incision in the region of the patient's obturator foramen and subsequently emerging through a vaginal incision. The needle 60R includes a handle 64R and a leading region 62R. Referring to FIG. 27, the leading region 62R includes a substantially blunt distal tip 63R and specially designed surfaces 67R and 65R suitable for mating with complementary surfaces on a dilator or connector (described in more detail below). Notably, in one aspect of the present invention, a novel needle of the present invention may utilize an eyelet in the distal region to afford a suture attachment to a sling or sling assembly without the use of a dilator.

As shown in FIGS. 15-18, the needle 60R has substantial structure in three dimensions, as opposed to, for example, the substantially flat needle shown in FIG. 1 (or an Emmet needle) that only includes substantial structure in two dimensions. Having substantial structure in three dimensions helps the surgeon pass the needle through the obturator foramen and subsequently through a vaginal incision by affording greater surgeon control. The handle of the needle allows the surgeon to move the distal end of the needle with an ergonomic wrist roll action FIGS. 15A, 16A, 17A and 18A show another embodiment of novel needle 60R' that is similar, but not identical to the needle 60R. The needle 60R' is also particularly suitable for passage on the right side of a patient's body, initially from an incision in the region of the patient's obturator foramen and subsequently emerging through a vaginal incision.

FIGS. 19, 20, 21 and 22 show another novel needle 60L according to the present invention. The needle 60L is particularly suitable for passage on the left side of a patient's body, initially from an incision in the region of the patient's obturator foramen and subsequently emerging through a vaginal incision. The needle 60L includes a handle portion 64L and a leading region 62L. Like the needle 60R, the needle 60R includes substantial structure in three dimensions.

FIGS. 19A, 20A, 21A and 22A show another embodiment of novel needle 60L' that is similar, but not identical to the needle 60L. The needle 60L' is also particularly suitable for passage on the left side of a patient's body, initially from an incision in the region of the patient's obturator foramen and subsequently emerging through a vaginal incision.

The instruments in FIGS. 15-22 are shown with indicator marks 66, 68 and 70. The indicator marks may be used by the surgeon to determine how far the need has been advanced into the patient. The indicator marks may, as examples, be mechanically or laser etched into the needle portion of the instruments. Marks may be placed at even spacings (e.g. every millimeter) to provide a visual measure of the distance the needle has been advanced. As an alternative, different regions of the needle may be color coded to provide a further visual indication to the surgeon of how far the needle has advanced into the patient.

Figure 20:
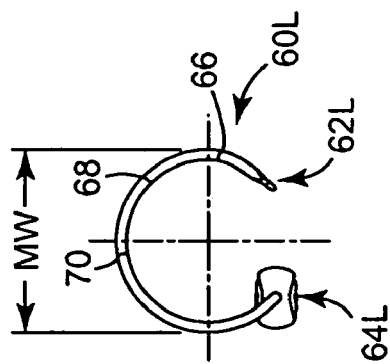
FIG. 20 is an end view of the needle of FIG. 19.
Figure 20A:
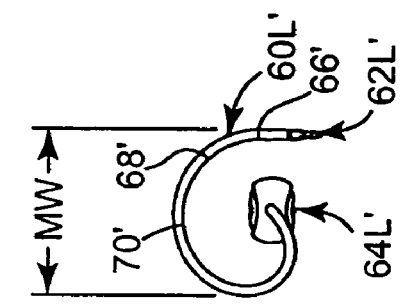
FIG. 20A is an end view of the needle of FIG. 19A.
Figure 20B:
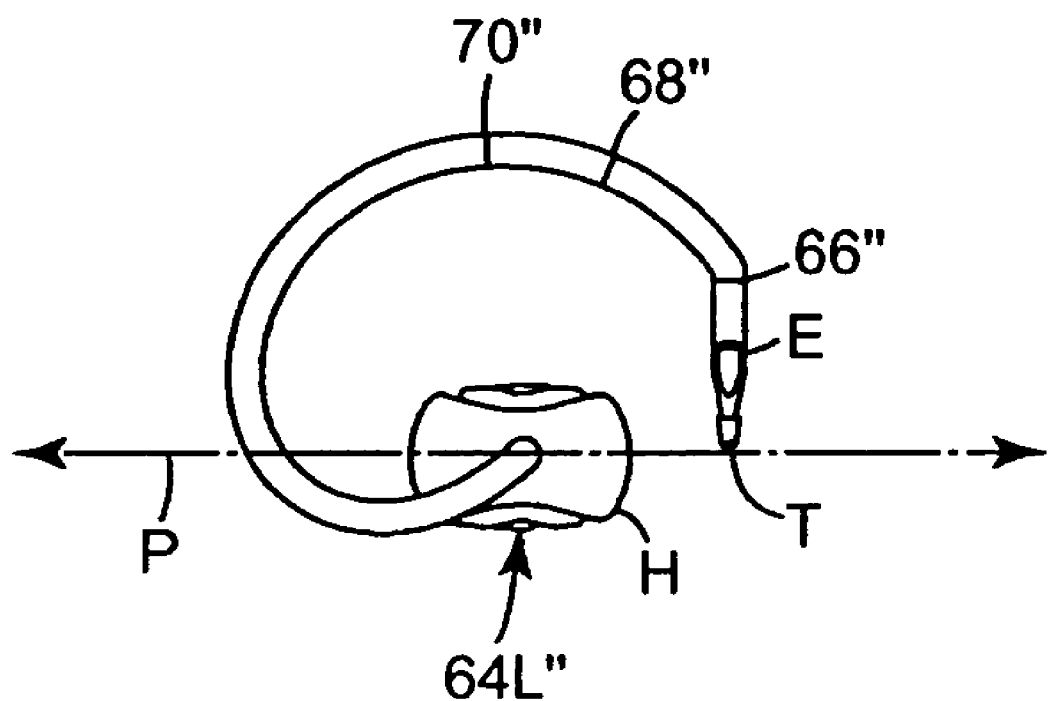
FIG. 20B is an end view of another embodiment of needle according to the present invention.
Figure 24:
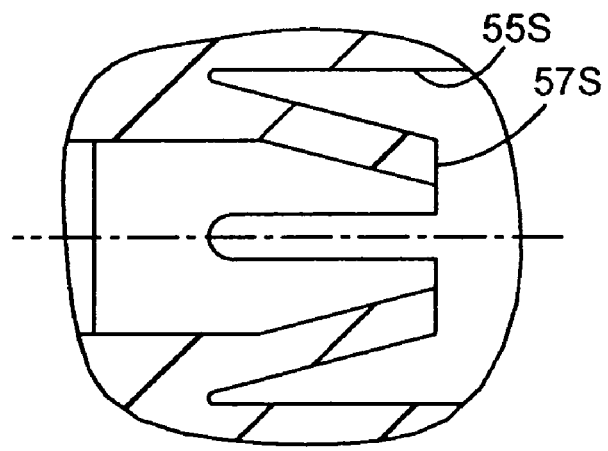
FIG. 24 is an enlarged, sectional view of an internal portion of the dilator of FIG. 23 in accordance with an aspect of the present invention.

Yet another embodiment of novel needle is shown in FIG. 20B. The novel needle 64L" is substantially similar to the needle 64L', except that the tip T of the needle lies substantially in the plane P of the handle H of the needle 64L". It is believed that such an arrangement of the elements may assist some surgeons in conjuring a mental image of the location of the tip T of the needle 64L" relative to the body while the needle is being passed through a patient outside the surgeon's direct vision. The arrangement of the tip and the handle affords visual feedback concerning the approximate location of the tip of the needle when the tip is not under direct vision. Instead of a snap-in feature for connection to a dilator, this needle 64L" includes an eyelet E for threading a suture so that the needle 64L" can be tied to an implantable material or assembly such as a knitted polypropylene sling with an associated sheath.

Figure 17:
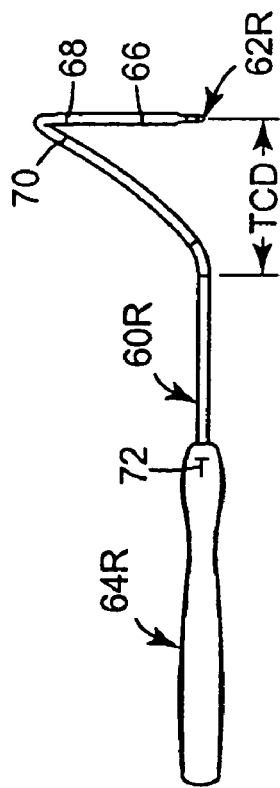
FIG. 17 is a front view of the needle of FIG. 15.
Figure 16A:
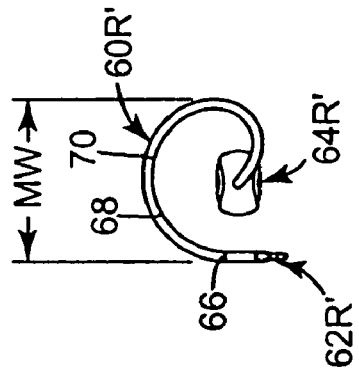
FIG. 16A is an end view of the needle of FIG. 15A.
Figure 18A:
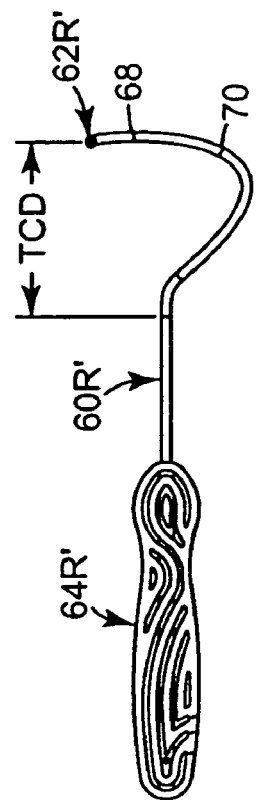
FIG. 18A is a bottom view of the needle of FIG. 15A.
Figure 15A:
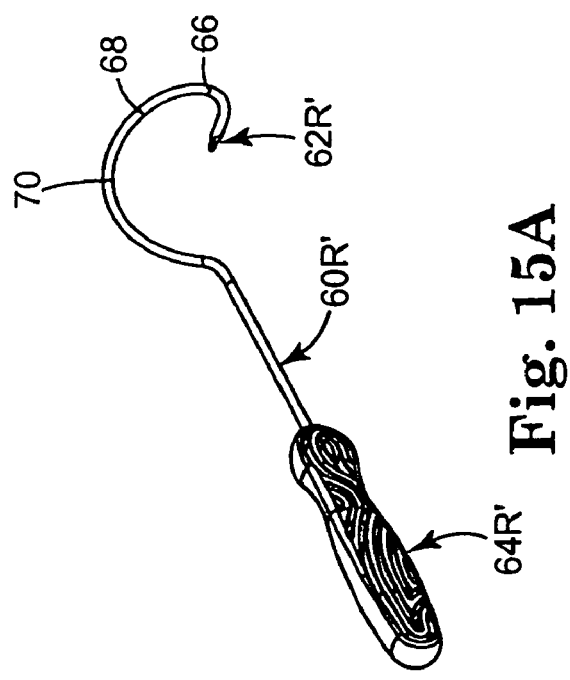
FIG. 15A is a perspective view of a surgical instrument particularly suitable for use on a right side of a patient's body, which needle is similar, but not identical to the needle of FIG. 15.
Figure 17A:
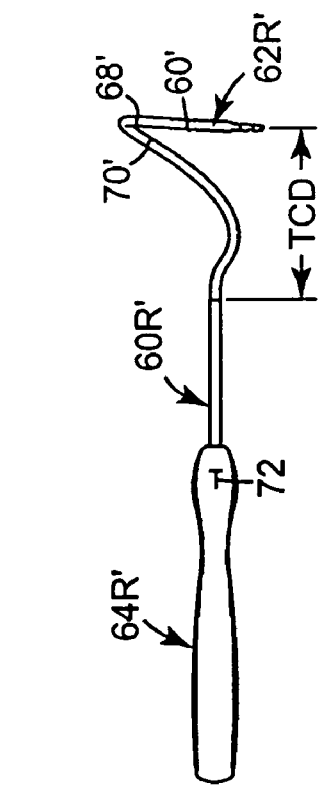
FIG. 17A is a front view of the needle of FIG. 15A.
Figure 22:
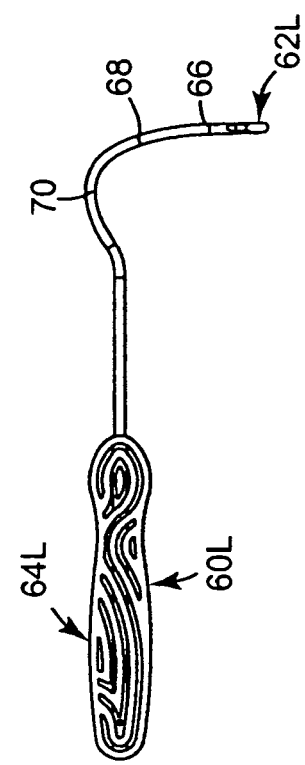
FIG. 22 is a bottom view of the needle of FIG. 19.
Figure 19:
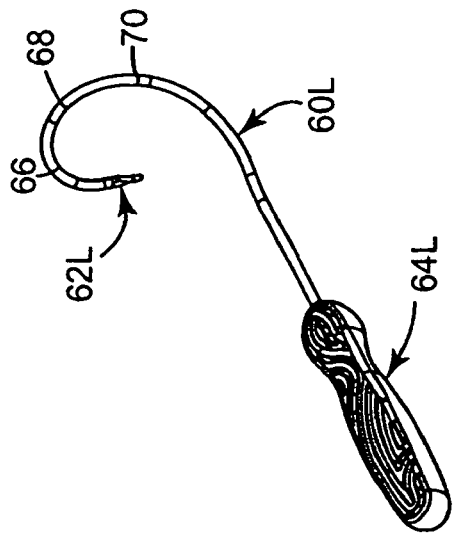
FIG. 19 is a perspective view of a surgical instrument particularly suitable for use on a left side of a patient's body, according to one aspect of the present invention.
Figure 21:
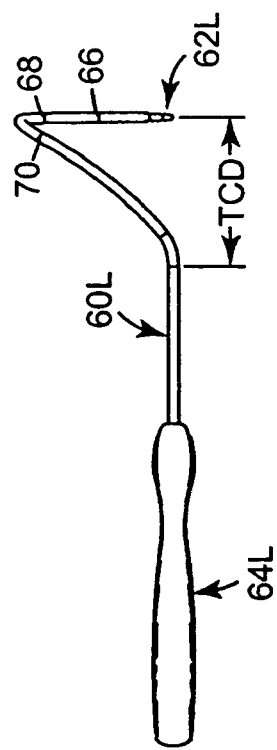
FIG. 21 is a front view of the needle of FIG. 19.
Figure 19A:
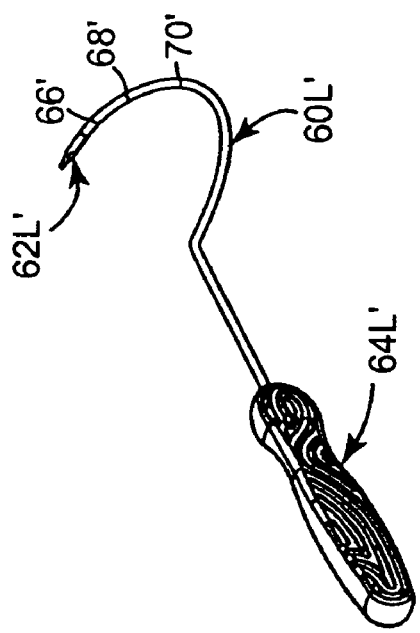
FIG. 19A is a perspective view of a surgical instrument particularly suitable for use on a left side of a patient's body, which needle is similar, but not identical to the needle of FIG. 19.
Figure 22A:
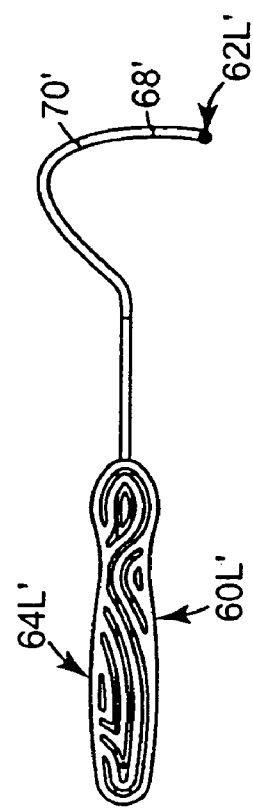
FIG. 22A is a bottom view of the needle of FIG. 19A.
Figure 21A:
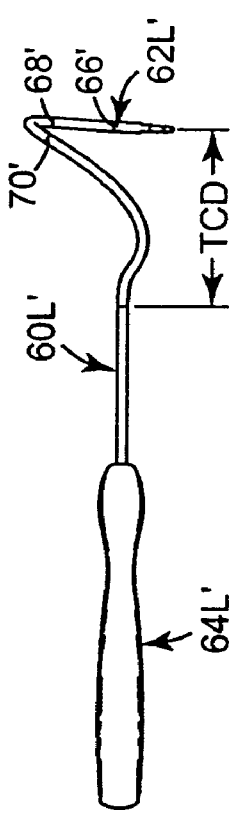
FIG. 21A is a front view of the needle of FIG. 19A.

Further, as can be seen by FIGS. 17, 17A, the handle of the instrument has been marked with an indicator 72 to provide a visual indication for the surgeon of the rotational location of the tip 62 of the needle. Here, the visual indication is the letter T on the side of the handle on which the needle ends.

Figure 63:
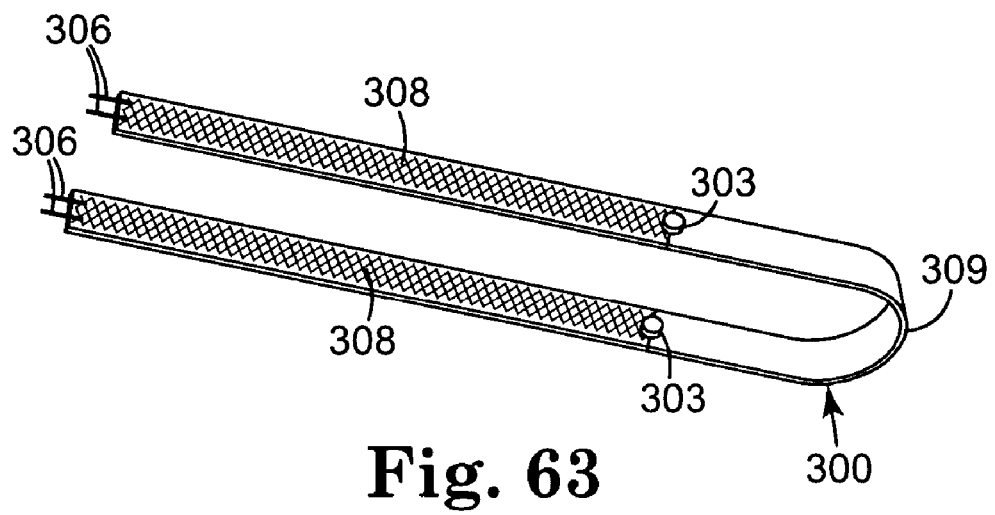
FIG. 63 is a perspective view of an alternative embodiment of sling assembly for use in accordance with the present invention.

FIGS. 63 through 67 show various embodiments of sling assemblies suitable for use in the present invention. These assemblies may be used in systems that do not include a dilator. FIG. 63 illustrates a sling assembly 300 having sutures 306 for threading through an eyelet of a needle to associate the assembly 300 with a needle. The assembly 300 may comprise a composite assembly with synthetic portions 308 and a non-synthetic mid portion 309 connected with fasteners 303.

Figure 64:
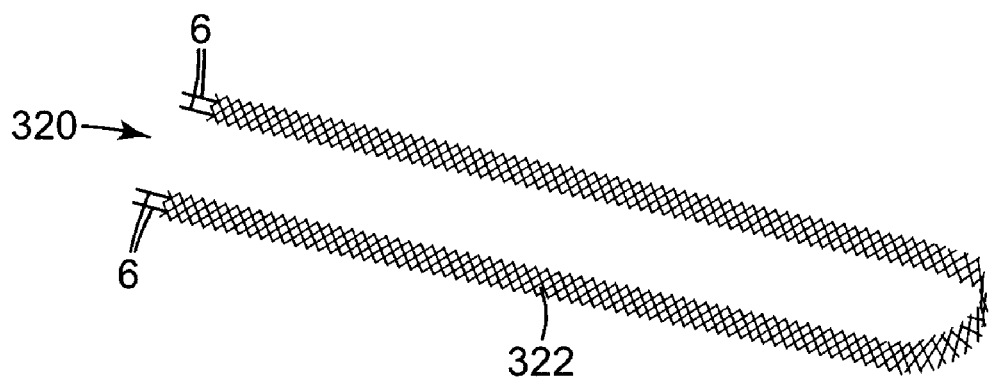
FIG. 64 is a perspective view of an alternative embodiment of sling assembly for use in accordance with the present invention, which assembly does not include a sheath.

FIG. 64 shows a sling assembly 320 comprising only a synthetic mesh material 322. Sutures 6 may be threaded through an eyelet of a needle to associate the assembly 320 with a needle. Optionally, a sheath may be added to the assembly 320, especially when the mesh 322 is elastic.

Figure 65:
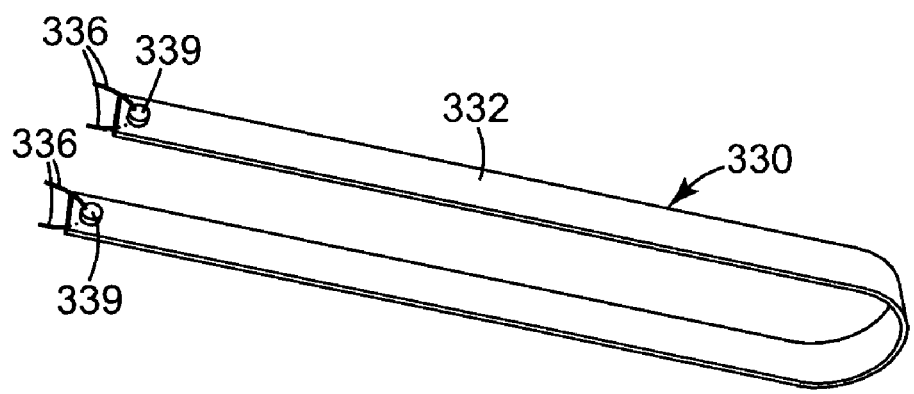
FIG. 65 is a perspective view of an alternative embodiment of sling assembly for use in accordance with the present invention.

FIG. 65 illustrates a sling assembly 330 comprising a non-synthetic sling 332. Sutures 336 may be threaded through an eyelet of a needle to associate the assembly 330 with a needle. Optionally, suture anchors or pledgets may be utilized to avoid suture pull through.

Figure 66:
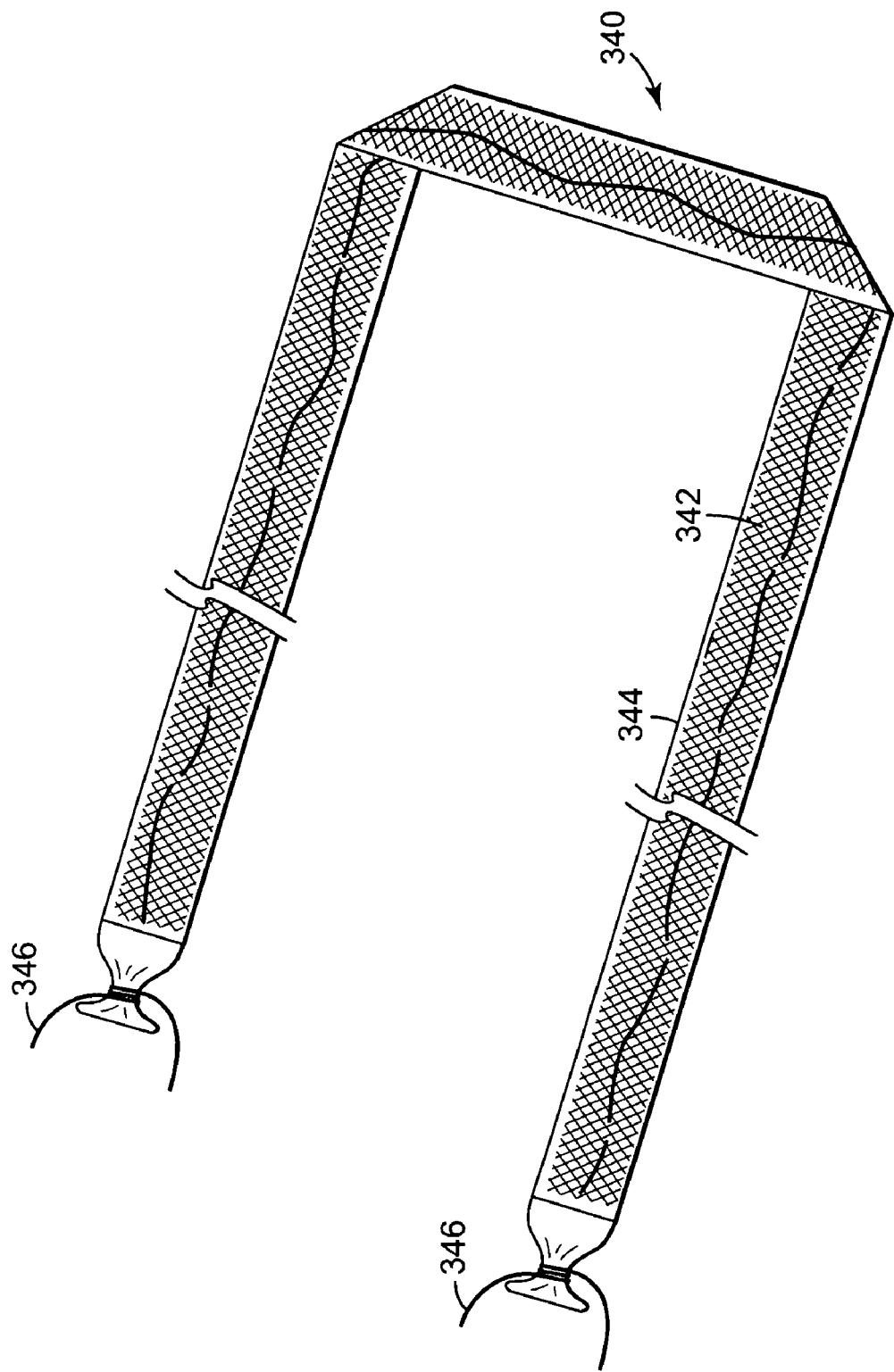
FIG. 66 is a top plan view of an alternative embodiment of sling assembly for use in accordance with the present invention.

FIG. 66 illustrates a sling assembly 340 comprising a sling mesh 342 and a sheath 344. In this embodiment, the ends of the sling mesh 342 may be attached to the ends of the sheath 340 by welding, suturing, or other suitable means. Sutures 346 may be tied about the ends of the sheath 344 to form a dilator-like structure for pushing tissue out of the way of the assembly 340 during implantation. The sutures 346 may be threaded through an eyelet of a needle to associate the assembly 340 with a needle. FIG. 66 also shows a tensioning suture, but this is optional and can be omitted.

Figure 67:
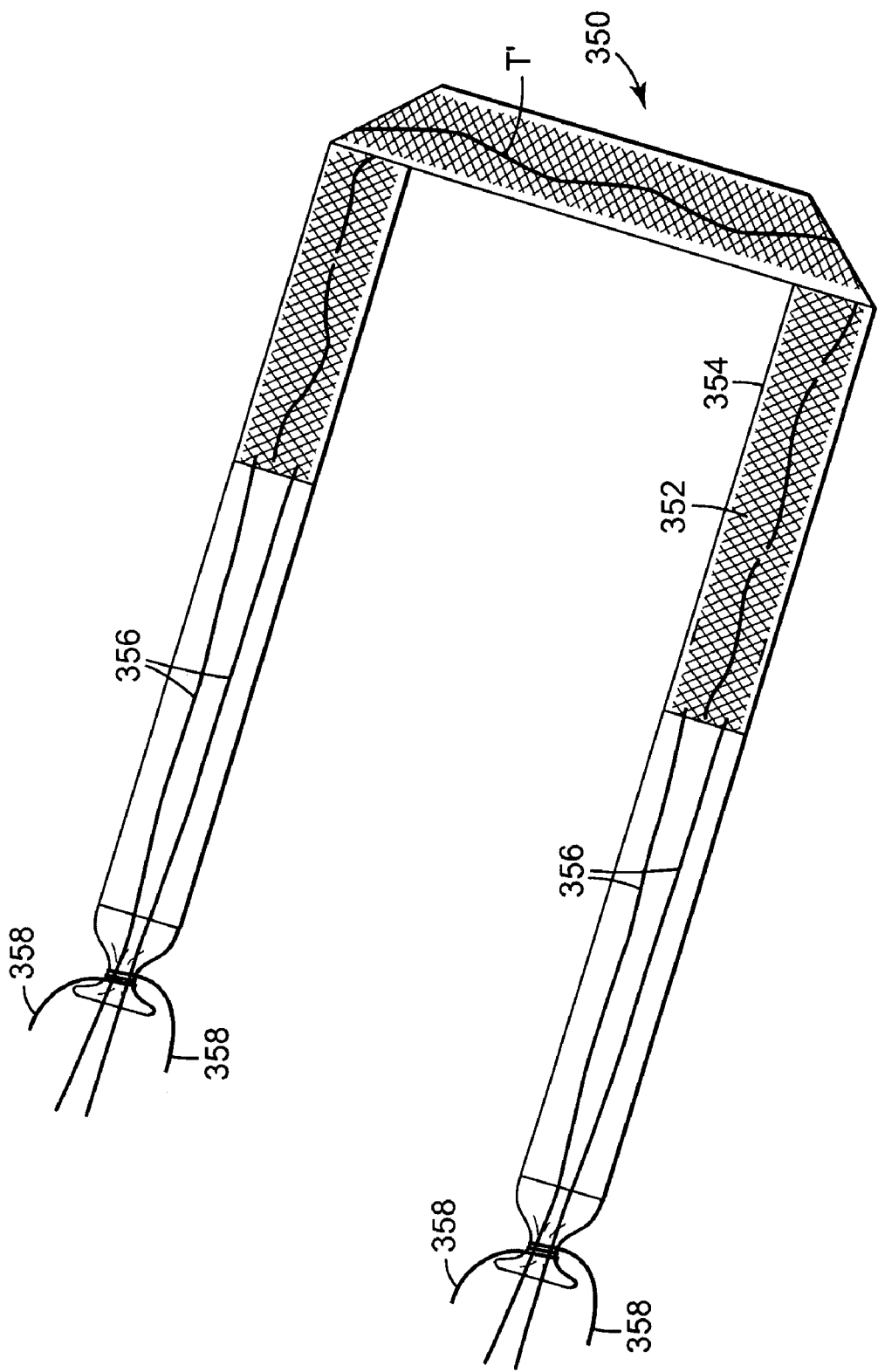
FIG. 67 is a top plan view of an alternative embodiment of sling assembly for use in accordance with the present invention.

FIG. 67 illustrates another sling assembly 350 comprising a synthetic mesh 352 and a sheath 354. Sutures 356 may be threaded through an eyelet of a needle to associate the sling 352 with a needle. Sutures 358 may be tied about the ends of the sheath 354 to form a dilator-like structure for pushing tissue out of the way of the assembly 350 during implantation. FIG. 67 also shows a tensioning suture T', but this is optional and can be omitted.

Figure 32:
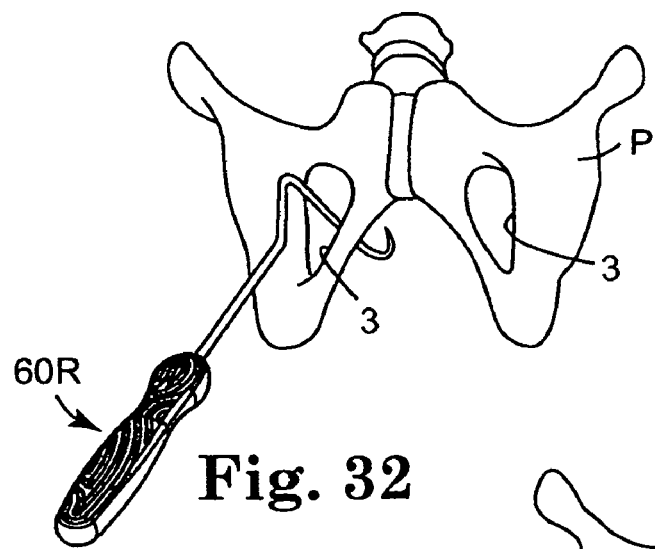
FIG. 32 is a schematic illustration of the relative positions of the patient's pubic bone and a novel needle according to the present invention, after at least partially inserting the needle.
Figure 33:
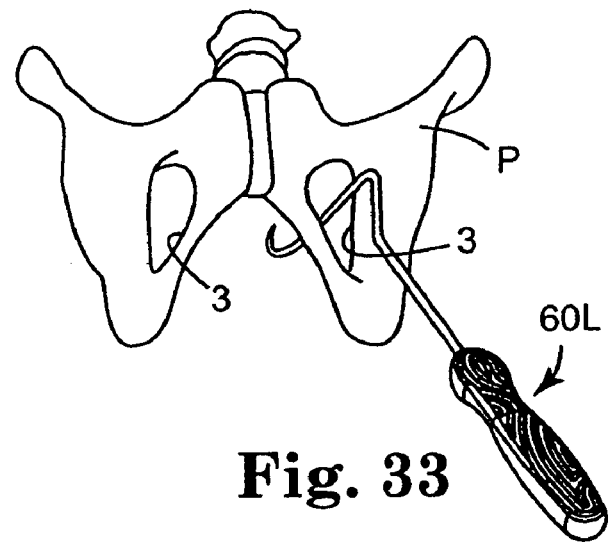
FIG. 33 is a schematic illustration of the relative positions of the patient's pubic bone and a novel needle according to the present invention, after at least partially inserting the needle.
Figure 34:
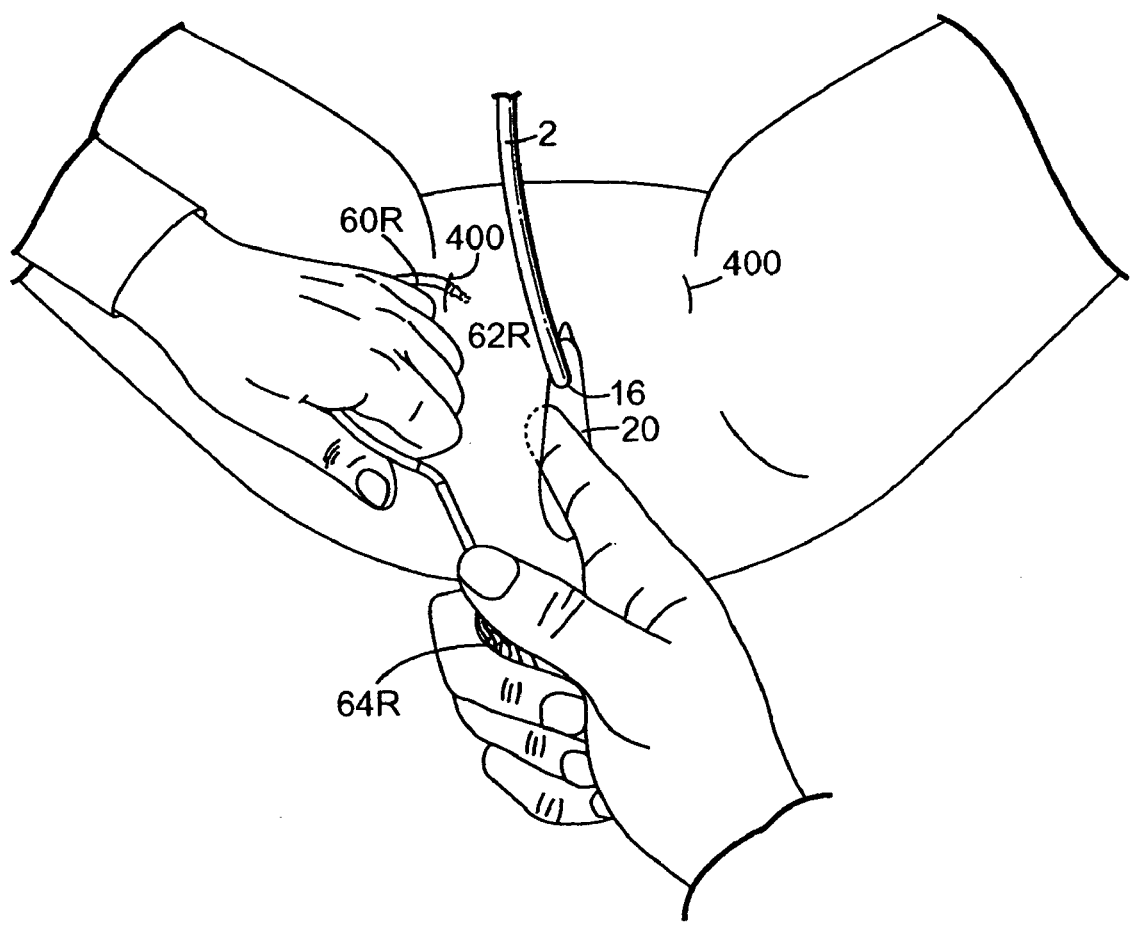

Preferably, the handles of the surgical instruments shown in FIGS. 15-20B includes indicia indicating the proper side of the patient. For example, the indicia may be any suitable information conveying word, symbol or depiction. The indicia may simply be "right" or "left." For those instruments designed for use on the right side of the patient, the indicia may include a drawing similar to FIG. 32. For the instruments designed for use on the left side of the patient, the indicia may include a drawing similar to FIG. 33.

The various embodiment of three dimensional needles described above preferably include a substantially straight spacer portion emerging from an end of the handle portion preferably along the handle axis. This helps afford convenient passage of the needle using an ergonomic wrist roll adopted by some surgeons. The three dimensional needles also include a structure that can be described as a variable spiral portion extending from the distal end of the straight spacer portion. As shown, the spiral portion is preferably variable as the angle of the spiral portion changes between the end of the extension portion and the distal end of the needle. The shape of the spiral portions help avoid over insertion of the needle into the body which helps avoid damage to the sensitive structures in this region of the body.

The variable spiral portions of the three dimensional needles have tissue clearance depth TCD of greater than about 0.5 inches and less than about 2.5 inches, more preferably the tissue clearance depth is between 0.75 inches and about 2.25 inches, more preferably it is between about 1.5 and 2 inches, and even more preferably it is about 2 inches. The tissue clearance depth TCD is the distance between the end of the extension portion and a point along an extension of the axis of the straight spacer portion which is defined by a line that is normal to the axis and that intersects the distal tip of the needle. The tissue clearance depth TCD helps space the distal tip of the needle from the distal end of the extension portion to reduce interference in needle passage by the distal end of the extension portion.

The variable spiral portions of the three dimensional needles have a maximum width MW that is preferably great enough to afford passage around the inferior pubic ramus and through the natural opening of the pubic bone, but small enough to avoid sensitive structure in this region of the body. Preferably, the maximum width MW is greater than about 1.25 inches and less than about 3 inches, more preferably, it is between about 2 and about 2.225 inches and more preferably, it is about 2.15 inches.

Referring to FIGS. 23, 24, 25, 25A and 26, there is shown a novel dilator 54S according to another aspect of the present invention. The dilator 54S includes a hole 90S for receiving a sling or a sheath or both in order to associate the dilator with a sheath.

Due to the more tortuous path associated with a transobturator route and the tighter radial passage, a shorter dilator is preferred to reduce tissue trauma and afford convenient, easy passage. Rotation of a helical needle can cause a substantially straight dilator to skid or plow through tissue instead of moving in a direction parallel to the longitudinal axis of the dilator. A shorter dilator will reduce tissue trauma associated with such plowing or skidding. Alternatively, a slightly curved or arcuate dilator may be used to reduce plowing or skidding.

The length L of a substantially straight dilator 54S is substantially short, preferably less than about 30 mm (1.2 inches) more preferably less than about 18 mm, 0.7 inches. The outermost diameter D of the dilator 54S is preferably less than about 6 mm 0.24 inches, more preferably less than about 5 mm, even more preferably, less than about 4 mm. The dilator 54S preferably has surfaces 51S that provide a smooth transition between the needle (e.g. 60L) and the sling assembly.

The angle theta is preferably less than about 15 degrees and more preferably less than about 12 degrees.

In one embodiment of the present invention, one substantially straight dilator 54S may be used with either a left or a right side needle. Preferably, such a combination includes a distal region of the needle that is substantially straight. This length (e.g. L" in FIG. 26A) is preferably short, preferably less than 0.9 inches, more preferably less than 0.8 inches, more preferably about 0.42 inches. In one embodiment, the length L' in FIG. 25 may be 0.3 inches.

Figure 26:
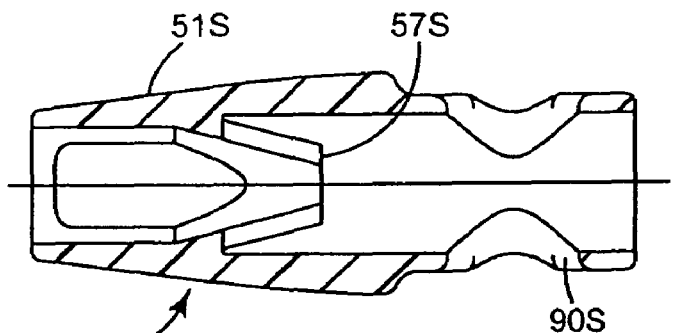
Figure 26A:
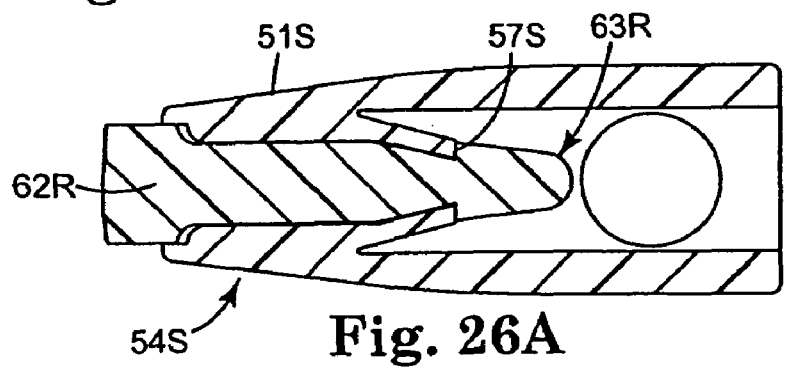
FIG. 26A is a sectional view illustrating a specially designed distal region of a needle inserted into the dilator of FIG. 25.

It is noted that the dilator is preferably capable of being "permanently affixed" to the needle. Preferably, the needle is attached to the dilator without a suture. FIG. 26A illustrates one example of a permanently affixed needle and sling assembly. By "permanent affixation", it is meant that it would be very difficult to manually separate the dilator from the needle after they have become permanently affixed. After implantation of the sling, to separate the sling from the dilator/needle subassembly, the surgeon cuts an end of the sling assembly (e.g. a cut is made through the mesh and protective sleeve) to separate the mesh from the needle/dilator subassembly. The connection between the needle and dilator preferably affords quick and convenient attachment of the dilator to the needle to avoid wasting time in the midst of a surgical procedure. The attachment should also be secure to avoid separation of the needle and dilator while the combination is passed through tissue.

To accomplish the preferred attachment, the dilator 54S includes an internal stop surface 57S that is complementary with specially shaped surfaces on a needle (e.g. 62R, FIG. 27). As best seen in FIG. 26A, the stop surface 57S is designed to engage complementary shoulder surface (e.g. 65R, FIG. 27) to achieve the desired convenient, but permanent affixation.

Also preferably, the needle is attached to the dilator without any screw-type connector. Preferably, the connection is a snap-fit, quick connection for secure, convenient use by the surgeon. Also preferably, the connection is a press on connection that does not require substantial rotation of elements (especially elements that are within the body) as such a connection is less likely to displace a needle or otherwise injure the patient.

Referring to FIG. 28, the dilators 54S may form a portion of a sling assembly that includes synthetic sling end portions 42A', sheaths 44A' covering at least some of the sling end portions 42A' and a non-synthetic mid-portion 45'. A composite sling assembly may be assembled by the surgeon or provided preassembled using the teachings or components of published U.S. Pat. Application Nos. 2002-0147382-A1 or 2002-0082619-A1, or U.S. patent application Ser. No. 10/335,119, filed Dec. 31, 2002.

In another aspect, the present invention comprises the ornamental design for a surgical instrument, as shown in FIGS. 39 through 45 and described in the Brief Description of the Drawings.

In another aspect, the present invention comprises the ornamental design for a surgical instrument, as shown in FIGS. 46 through 52 and described in the Brief Description of the Drawings.

The broken line showing in FIGS. 39-52 are for illustrative purposes only and form no part of the claimed design.

The above-described surgical instruments may be disposable or reusable. Optionally, portions of the surgical instrument may be reusable (sterilizable) and other components may be disposable.

EXAMPLES OF SURGICAL PROCEDURES

Several methods are contemplated herein. Although the methods of use as disclosed herein generally relate to female incontinence conditions and treatments/procedures, male incontinence conditions and treatments/procedures are also included within the scope of the present invention. Further, the term "urethra," with respect to sling positioning, is used for brevity and reader convenience. It should be noted that the present invention is particularly suitable for placing a sling in a therapeutically effective position. The method may be utilized to support a variety of structures at different anatomical locations. Variations of these methods may occur due to individual surgeon's techniques or a patient's particular anatomy.

Referring to FIGS. 4 through 10, a preferred embodiment of surgical procedure is disclosed. The present invention utilizes an obturator passage of the needle, preferably in a direction from the anterior to the posterior side of the pubic bone. An obturator approach affords a sling procedure where previous scarring in the region of the retropubic space or other anatomical features would prevent or restrict a traditional pubovaginal sling procedure. An obturator approach is also likely to avoid bladder perforations, a possible but rare complication with some prior art pubovaginal procedures. It may also be more convenient to conduct a concomitant repair (e.g. cystocele repair) with a sling inserted with a side approach as the sling is placed in a more horizontal position (e.g. see FIGS. 9 and 10) than the U-shaped sling procedures of the prior art.

Initially, the patient is placed under local, spinal or general anesthesia. A catheter 2 (e.g. Foley) may be inserted through the urethra 16. A small incision (e.g. a transverse incision) is made in the anterior vaginal wall 20 of a patient followed by a transurethral dissection. The amount of dissection may vary according to surgeon preference. Preferably, dissection is sufficient to allow the surgeon's finger to meet the end of the region 58 of the needle 60 just after it passes through the obturator fascia.

Two small stab incisions 400 are also made near the obturator fascia to afford needle entry. Notably, the precise location of the stab incisions 400 may vary according to surgeon preference. For example, some surgeons may place the incision adjacent the obturator opening of the pubic bone. Other surgeons may slightly offset the incision in order to use the bias provided by the patient's tissue to urge the tip of the needle in a direction toward the posterior surface of the pubic bone.

Referring to FIG. 4, the end of region 58 of needle 60 is shown just passing an incision 400 on the patient's right side. The surgeon's finger is initially placed in the vaginal incision sufficient to meet the end of region 58 of the needle 60 after it passes through the obturator fascia and the obturator foramen 3 (see FIG. 9). A path for the needle 60 through the obturator foramen 3 that is substantially free of vascular and nerve passages is selected. To select the path, the surgeon preferably initially identifies the anatomical structures of the pelvis such as the ischial tuberosity and obturator foramen 3 by palpation of the tissue.

Figure 5:
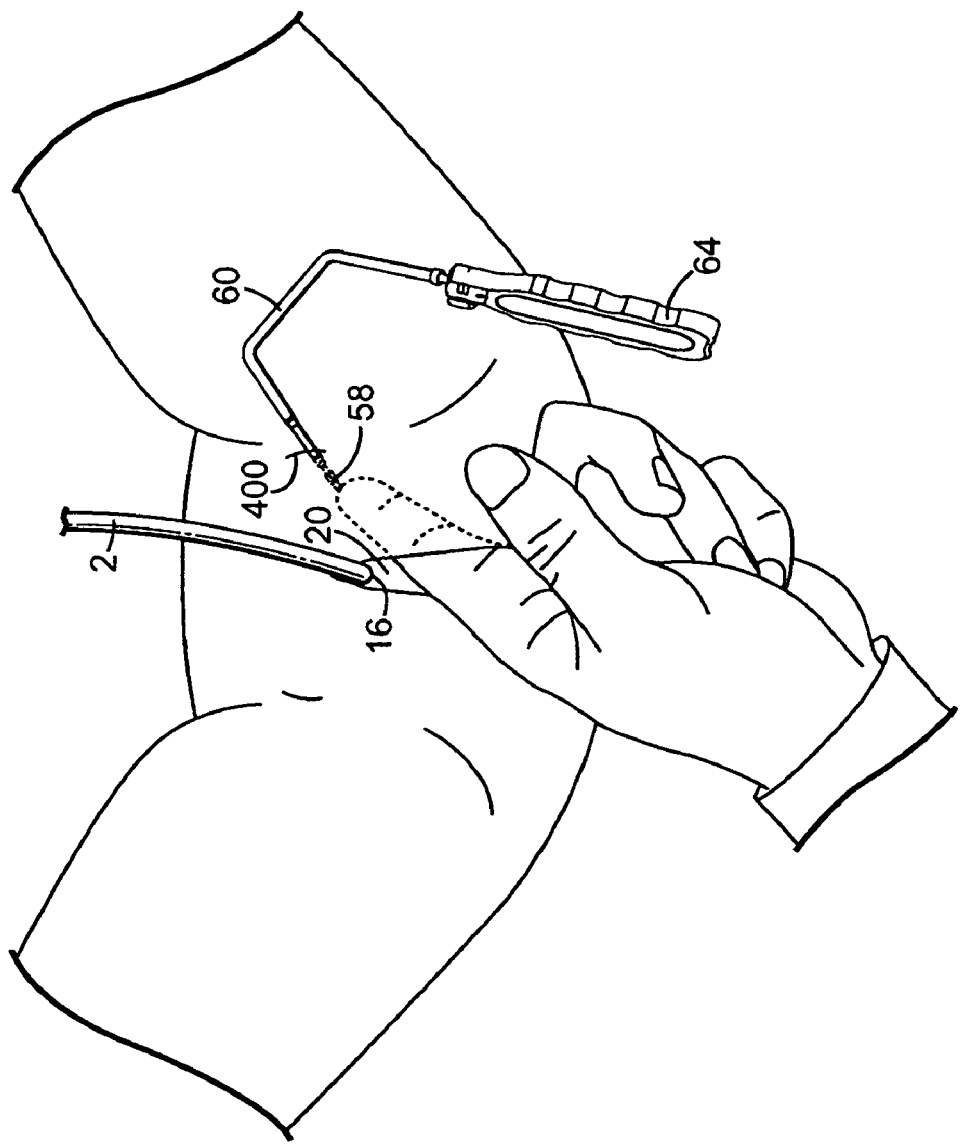

If optional handle 64 is used, it may be adjusted relative to needle 60 according to surgeon preference and securely associated with the end 62 of the needle 60. FIG. 5 shows the end of region 58 of needle 60 just passing an incision 400 on the patient's left side.

Preferably, the surgeon seeks to use the posterior portion of the patient's pubic bone as an anatomical guide to controllably move the tip of region 58 of the needle toward the vaginal incision and to help avoid damaging structures. The surgeon exploits the tactile feel provided by the posterior portion of the pubic bone to controllably pass the tip of the needle 60. This approach is preferred as it helps keep the needle 60 away from the bladder and other vulnerable tissues.

Figure 6:
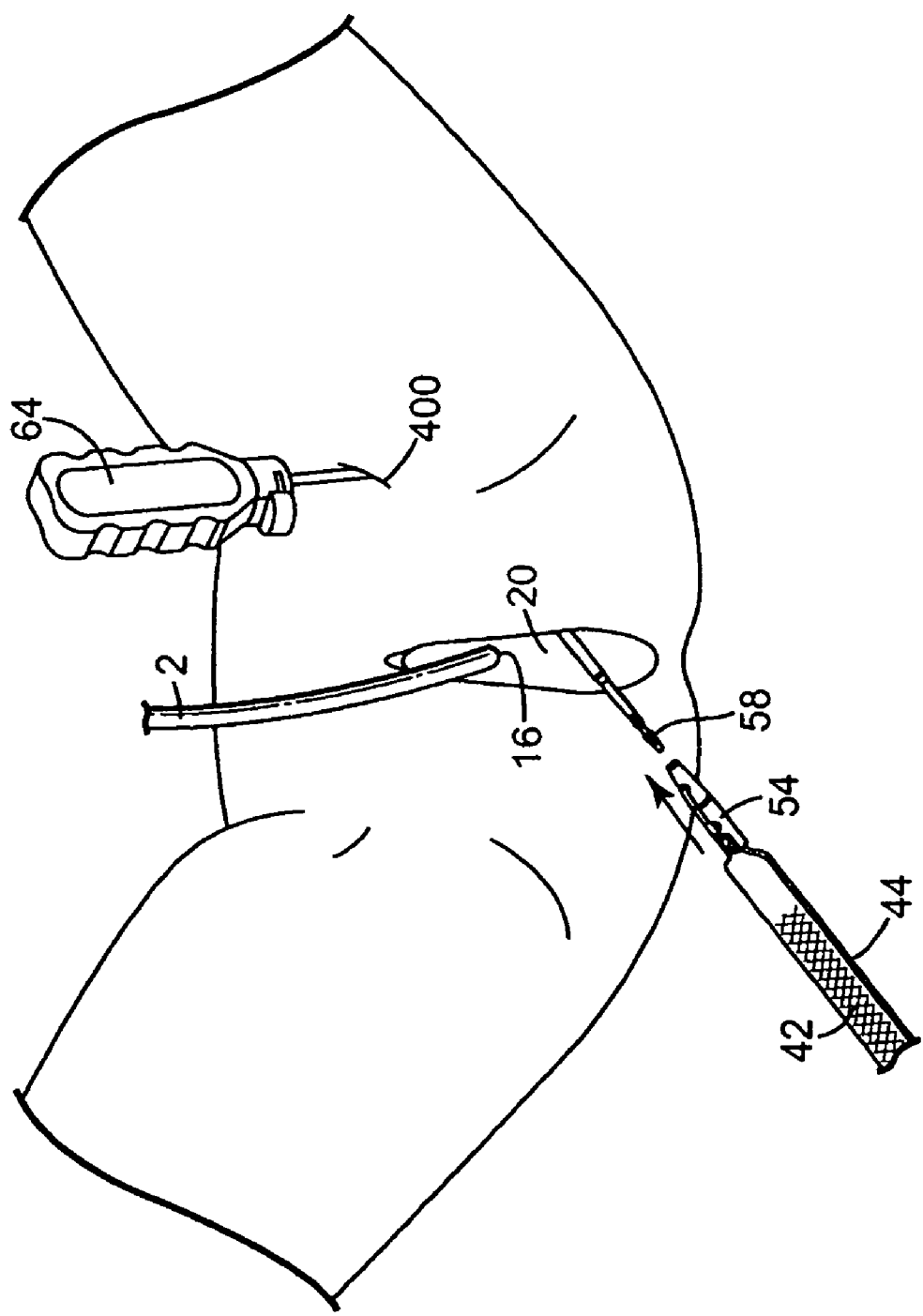

FIG. 6 illustrates the needle of FIG. 5 as it emerges from a vaginal incision. The shape and size of needles 60 help provide precise passage of the needles 60 to the vaginal incision. The steps described above are repeated as needed for both sides of the urethra 16. FIG. 6 also illustrates one side of a sling assembly 46 prior to association with the needle 60.

Figure 7:
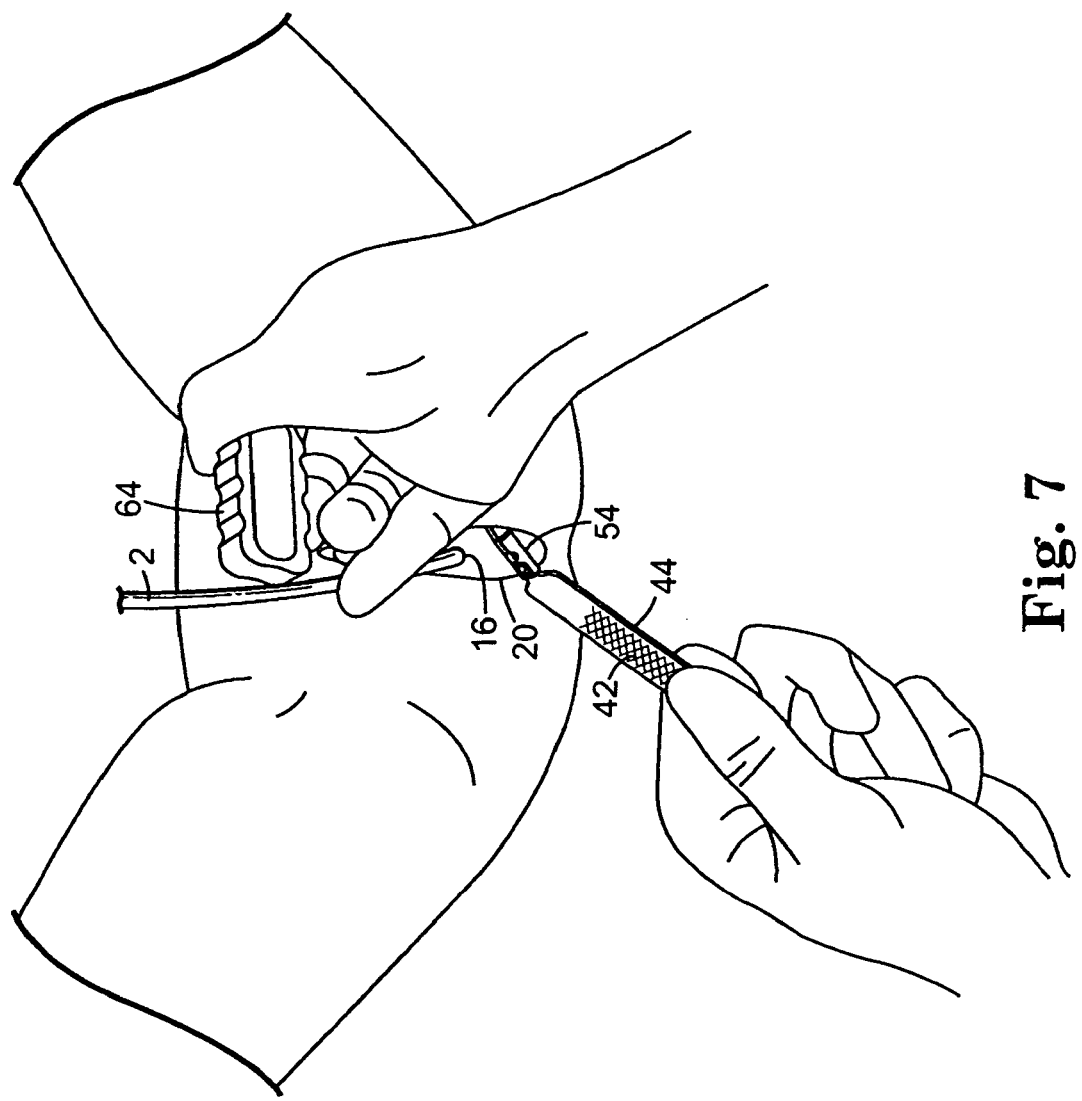

FIG. 7 is a perspective view of one side of a sling system after it is associated with needle 60. The dilators 54 of the sling assembly 46 are preferably snapped irreversibly into place on the needles 60 for a secure connection. Next, if a synthetic sling assembly is used, the plastic sheath 44 is oriented so that an optional center orientation indicia (e.g. a blue mark) is facing away from the surgical field, toward the surgeon.

After the dilators 54 are attached to the needles 60, the sling assembly 46 is properly oriented so that the sling assembly 46 is not twisted when attached to the dilators 54. After the dilators 54 and sling assembly 46 are properly positioned, dilators 54 and sling assembly 46 are pulled through the tissues of the patient.

Figure 8:
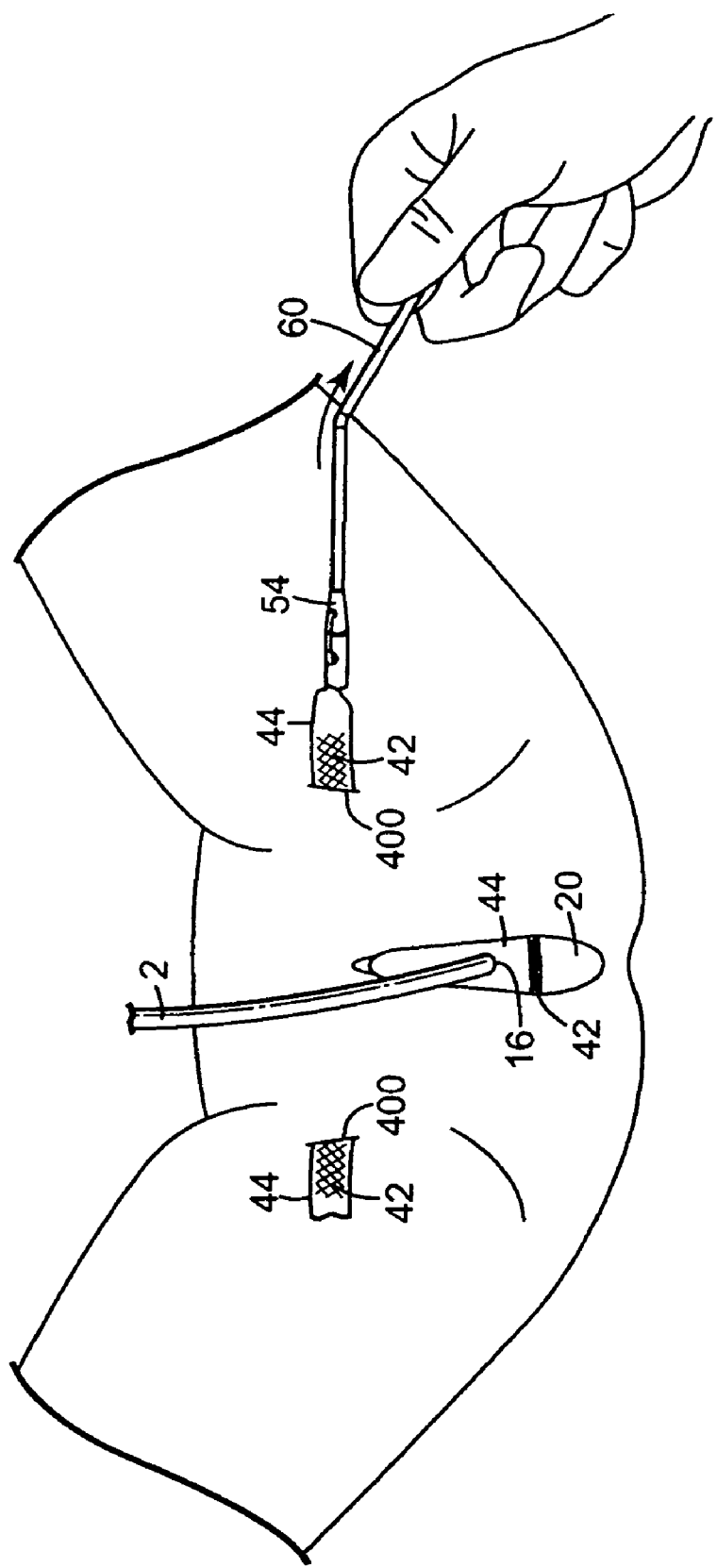

Referring to FIG. 8, once the dilators 54 are securely attached, the needles are pulled through the incisions 400, taking care to avoid contact with sensitive tissue. The sling is then clamped with surgical clamps (not shown). During this portion of the process, the attached dilators 54 and sling assembly 46 are atraumatically pulled through the needle paths, advancing the sling assembly 46 adjacent to and beneath the urethra 16 or target site. A portion of each end of the sling assembly 46 extending beyond the incisions 400 is clamped and then cut to release the needles 60 and attached dilators 54.

The sling is placed in a therapeutically effective position. FIGS. 9 and 10 show one example of a therapeutically effective position. Other positions are contemplated herein. The precise anatomical position will depend upon a variety of factors including the type and degree of anatomical damage or insufficiency, location of significant scar tissue, whether the sling procedure is combined with other procedures and other surgeon decisions. Typically, the sling is placed midurethra, without tension, but in position to support the midurethra. Alternatively, the sling could be placed to support the bladder neck and/or UV junction.

Once the sling assembly 46 is carefully positioned under the midurethra or target site to provide sufficient support to the target site, the overlapping portion of the sheath 44 located near the center of the sling assembly 46 and an optional tensioning member (i.e. tensioning filament) may then be used to center and properly position the sling assembly 46 under the midurethra. The sheath 44 is then removed.

Sling tension may be tightened by placing a device, such as a clamp across one or both ends of the sling 42. Generally, the surgeon grasps the mesh and tensioning filament together adjacent the incision 400 and pulls to increase the degree of tightness of the mesh.

After the dilators 54 are trimmed off, the plastic sheath 44 is removed from the sling mesh 42 by pulling on both sides of the sheath 44, preferably one at a time. Optionally, to avoid overtightening the sling mesh 42 while removing the sheath 44, a forceps or other blunt instrument may be placed between the sling and the urethra.

FIGS. 9 and 10 illustrate one embodiment of the final placement of the sling 42 relative to anatomical structures such as the pubic bone, urethra and vagina. The sling is flatter than the U-shaped slings of the prior art which extend to the rectus fascia of the patient's abdomen.

In another embodiment of the invention, shown with reference to FIG. 11, a method includes the steps of providing a surgical kit comprising at least one guide needle 60 constructed for an obturator approach, and at least one sling transport needle 604 with a sharp tip, a sling 610 attached to the sling transport needle 604, and a dilator 54 having tip receiving surfaces for receiving the sharp tip of the sling transport needle 604. The needle 60 has a relatively small diameter (e.g. less than 4 mm). The method includes the steps of creating at least one vaginal incision, creating two obturator stab incisions, and initially passing a guide needle 60 through the obturator incision and then through the vaginal incision. The dilator 54 is then attached or associated with the needle 60.

Needles 604 are initially guided through a vaginal incision and toward one of the obturator incisions 400. Guiding the sharp tip of the large sling transport needle 604 in this fashion is believed to help avoid contact between the sharp tip of needle 604 and sensitive structures. Optionally the adapter with receiving surfaces may be integrally formed in the needle 604 to avoid the need to separately attach the adapter to the needle 604.

FIG. 4A shows an alternative step according to an aspect of a method according to the present invention. This illustrates a method wherein the needle 60 of FIG. 1 is initially inserted through a vaginal incision and then emerges from a skin incision. In this embodiment, the sling assembly may then be attached to the end of the needle previously occupied by a removable and repositionable handle 64. The handle 64 may then optionally be placed on the other end of the needle 60 to assist the surgeon in passing the sling assembly and needle through the body. This is shown by the arrow in FIG. 4A adjacent the dotted line showing of the handle 64.

The method preferably includes the step of removing the handle 64 and attaching an end of the sling assembly to the region of the needle previously occupied by the handle 64. The needle tip and attached sling assembly are then passed completely through the body, in substantially the same direction as the initial insertion, to place one side of the sling assembly. As a result, it can be seen that the needle 60 is a universal needle (i.e. one that can be utilized for either an "outside-in" surgical approach or an "inside-out" approach).

Referring now to FIGS. 31-38, there is shown another embodiment of method according to the present invention. This embodiment is believed to be suitable for patients under local, regional or general anesthesia. This embodiment utilizes needles specially shaped for use on a predetermined side (e.g. right or left) of the patient.

A small incision may be made in the anterior vaginal wall followed by pariurethral dissection. Two small stab incisions are also made above the obturator foramen for instrument passage.

The patient is preferably placed in a modified lithotomy position with hips flexed, legs elevated. The bladder is emptied and a weighted vaginal retractor may be used.

The surgeon palpates the inferior portion of the ischiopubic ramus, palpates the edge of the bone and notes where the ischiopubic branch gets wider and the obturator membrane is tactily sensed. Just below this location and lateral to the bone is a preferred mark for the skin incisions. The surgeon preferably confirms that both marks lie in a straight line approximately at the level of the clitoris.

In the anterior wall of the vagina, the surgeon may draw a vertical mark approximately 0.5 cm below the meatus. The incision may be approximately 2 cm in length. An Allis forceps may be placed on the incision margin to expose the incision.

The surgeon incises the vaginal wall and extend the dissection laterally (pariurethral) with, for example, a Metzenbaum scissors. The surgeon then may dissect the pariurethral attachment to the vagina. The surgeon may then insert the tip of a blunt instrument (e.g. the Metzenbaum scissors laterally), spread and advance the scissors until the tip of the scissors touches the inferior portion of the bone (about 1-1.5 cm). This may be accomplished bilaterally. The vaginal dissection is preferably large enough for a finger tip to enter in both directions.

The instrument is then passed through the obturator foramen. The surgeon preferably palpates the interior portion of the ischiopubic ramus, palpates the edge of the bone and preferably moves his or her finger cephalad until muscle firmness is felt. Just below this location and lateral to the bone may be the mark for the skin incisions. The surgeon may confirm that both marks lie approximately in a straight line at the level of the clitoris.

The surgeon may then insert the index finger into the vaginal dissection and probe to the ipsilateral outer obturator foramen mark to confirm needle path. The surgeon makes a small vertical skin incision on the same side over the skin mark denoting the foramen. If patient side specific instruments are used (e.g. those shown in FIGS. 15-22), the instrument designated for the patients left side 60L may be removed from the package. The surgeon points the instrument tip perpendicular to the skin and proceeds to the level of the obturator fascia.

Figure 35:
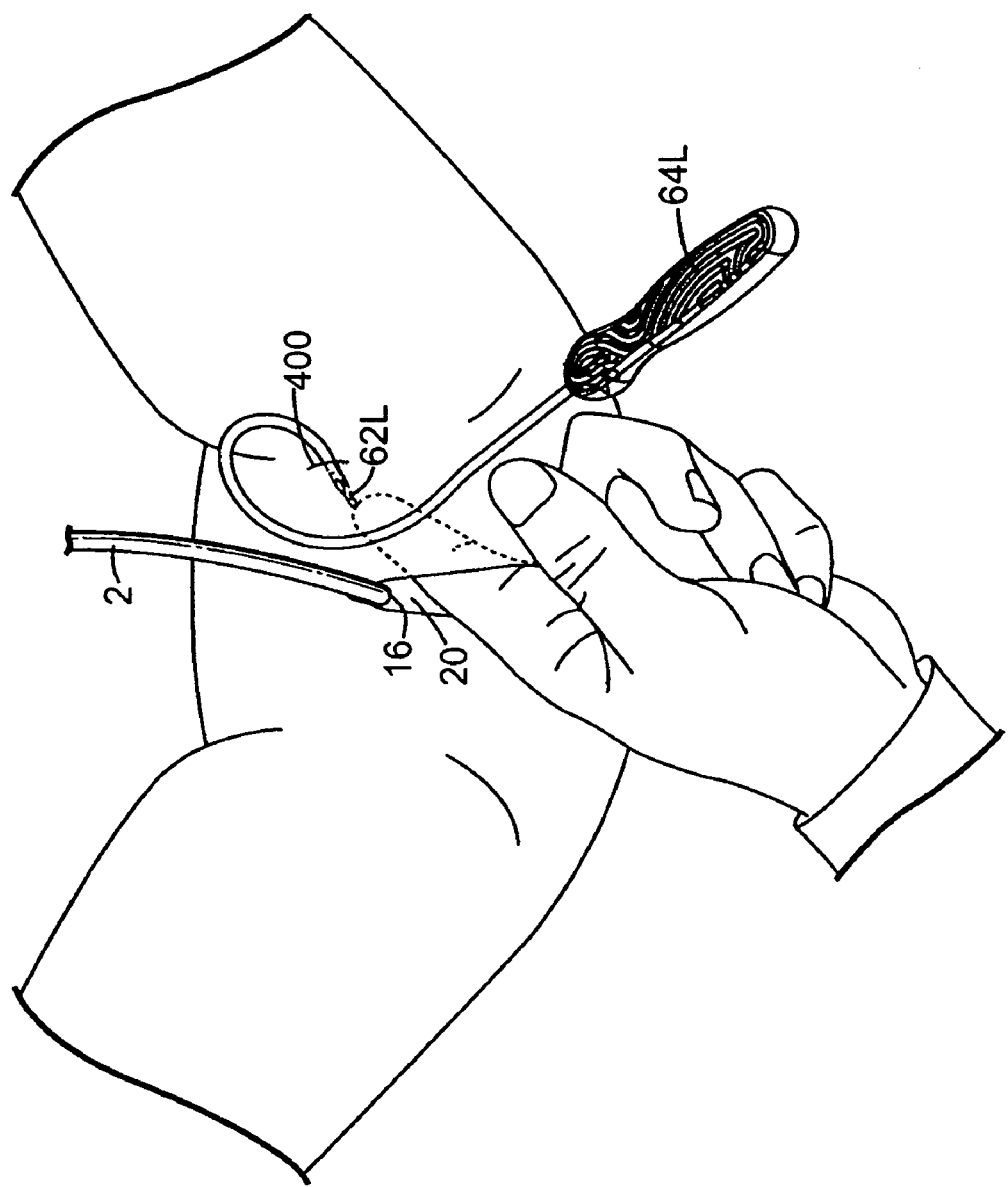

With a finger in vaginal incision, the surgeon moves the finger laterally to meet the needle tip (see FIG. 35). When passing the needle 60L on the patient's left side, the surgeon preferably keeps his or her right hand on the needle handle and left index finger in the vaginal incision. The surgeon's left thumb may optionally be on the outside curve of the needle 60L to control the needle movement. The surgeon's left thumb preferably pushes the needle through the muscles and obturator fascia. The needle tip preferably penetrates until resistance of the tissue stops—about 0.5 cm.

The surgeon then preferably immediately locates the ischial pubic ramus with the needle tip 62L and rotates the needle handle 64L (see FIG. 33) to allow the needle to follow the posterior ischial pubic ramus surface. The index finger tip should palpate the needle tip. If not, the surgeon should move the needle to meet the finger tip. If the needle tip cannot be located, then the needle should be withdrawn just behind the ischial pubic ramus and advanced again.

Figure 36:
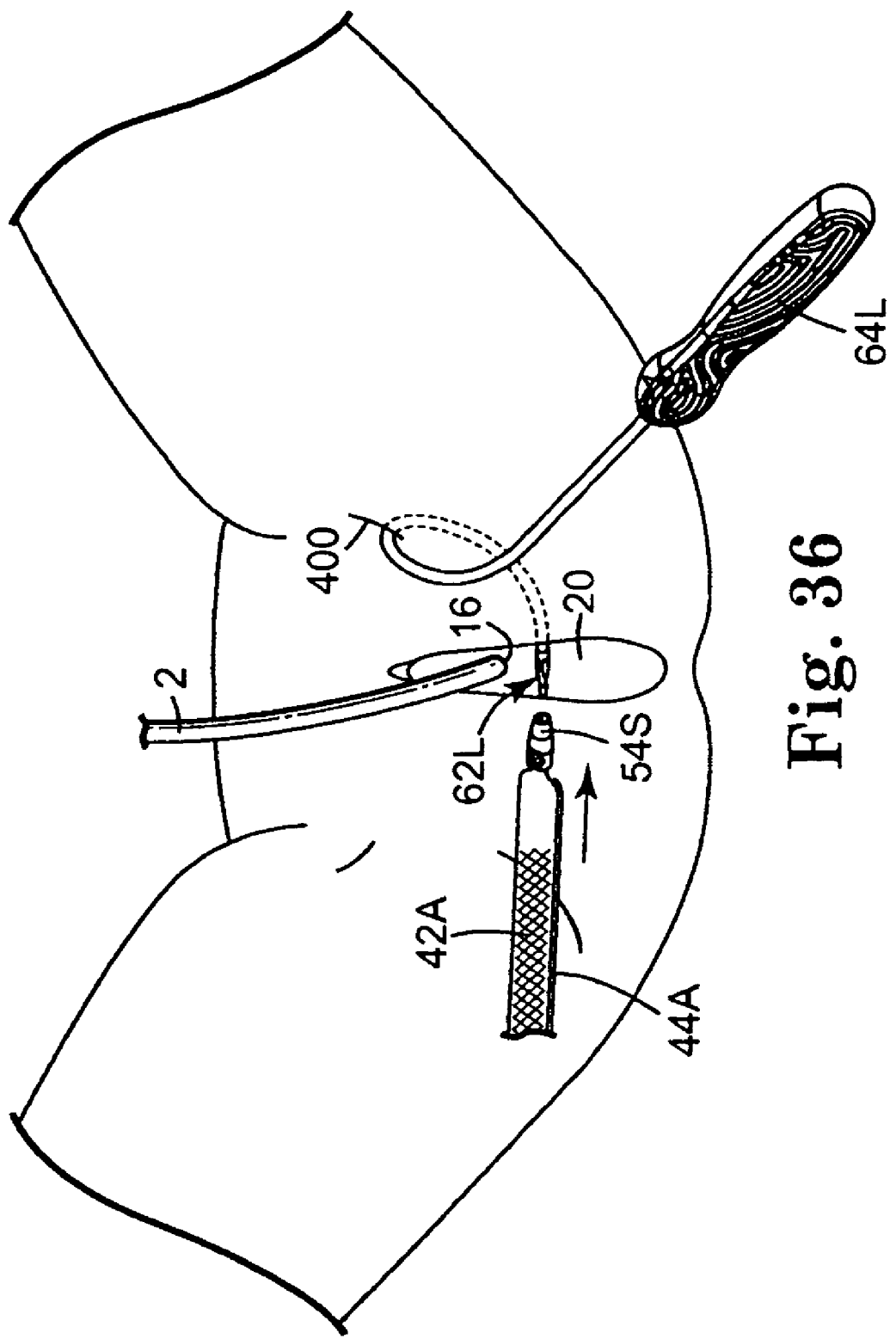
Figure 37:
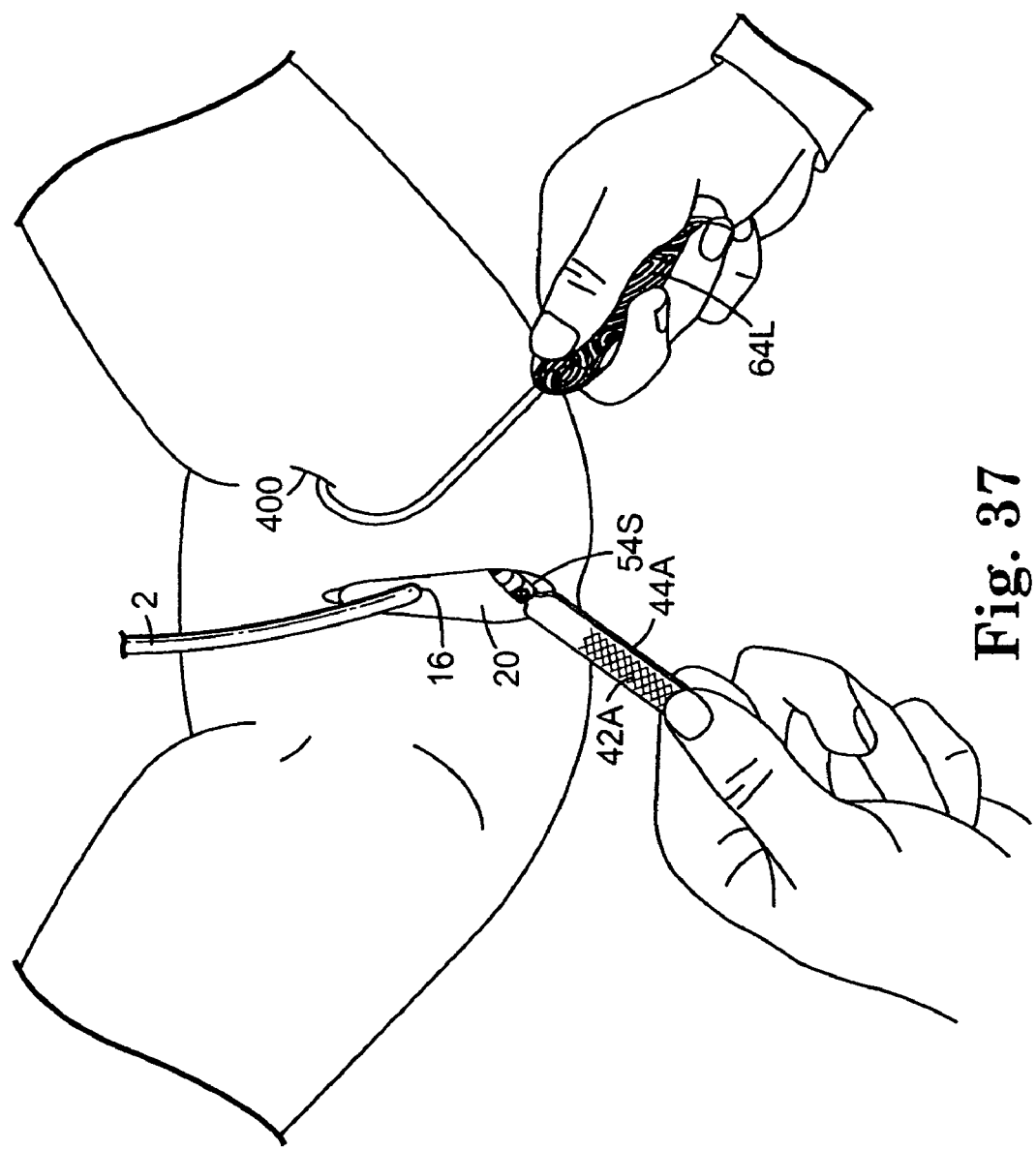

Using the index finger, the surgeon preferably guides the instrument tip medially towards the vaginal incision until the instrument tip extends through the incision (see FIG. 36).

The above steps are repeated on the patient's right side. See FIGS. 32 and 34. Cystoscopy may not be required but can be done at the surgeon's discretion.

The surgeon then attaches the dilating connectors (that are pre-attached to the sling mesh) to the regions of the instruments 60L and 60R that emerge from the vaginal incision. One dilating connector 54S should be attached to each of the instruments 60L and 60R on the regions protruding from the vagina. If optional colored markings or indices are used on the sling assembly, the surgeon orients these markings on the sheath facing outward, away from the urethra 16. The surgeon may use the markings to help ensure that the sling mesh lies flat and that the mesh is not twisted prior to attaching the second dilator 54S as the dilators cannot be removed once they are snapped into place.

Figure 38:
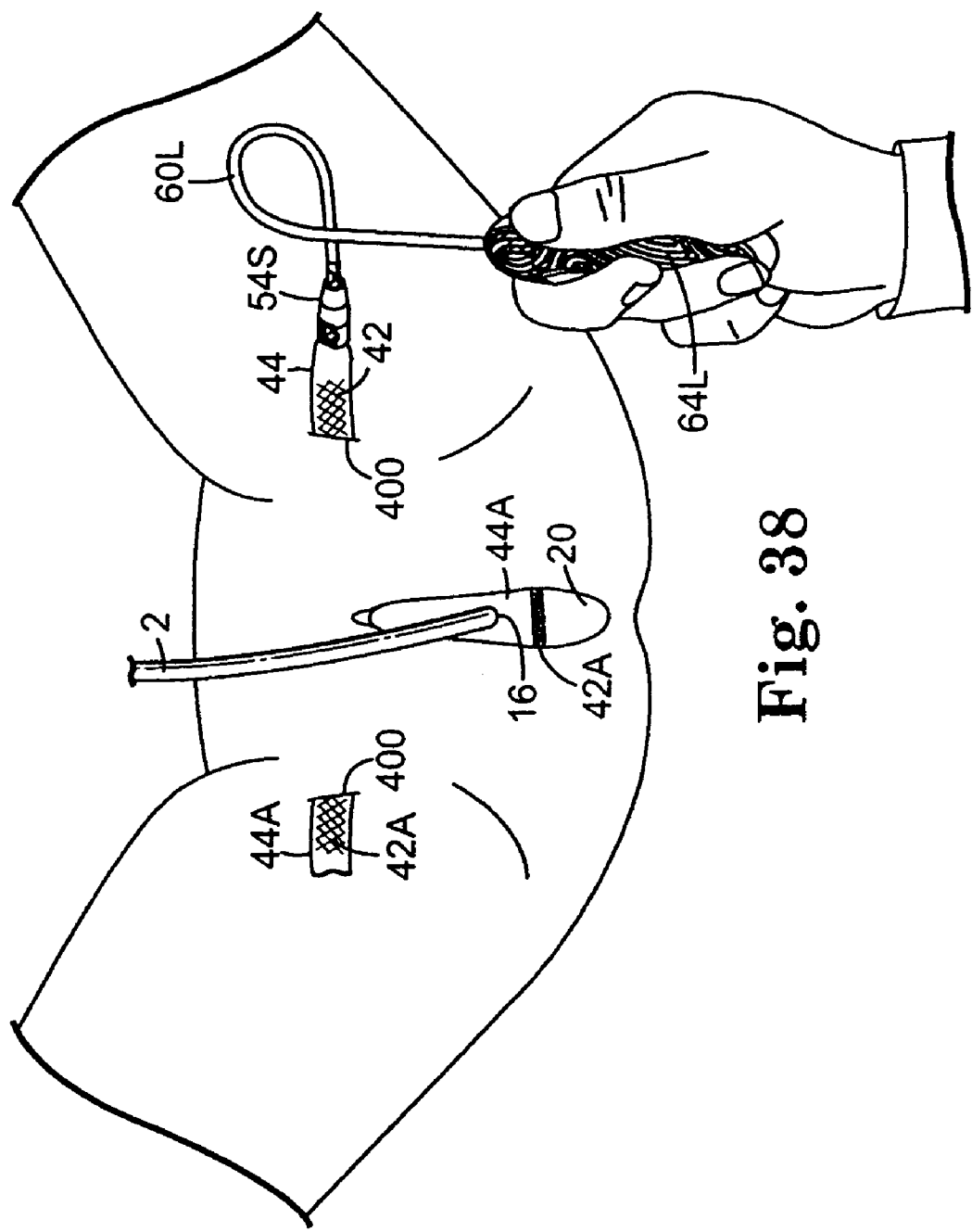
Figure 39:
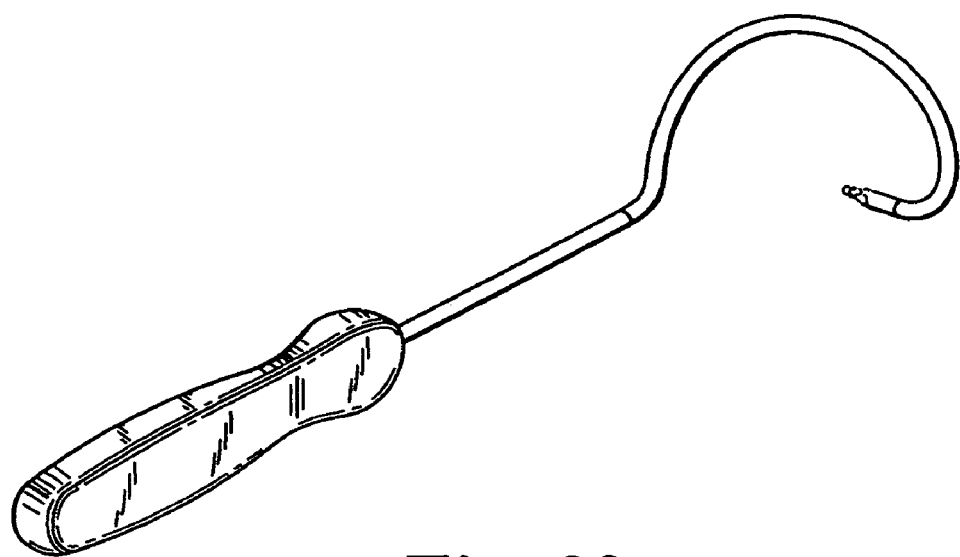
FIG. 39 is a perspective view of a design of a surgical instrument according to another aspect of the present invention.
Figure 40:
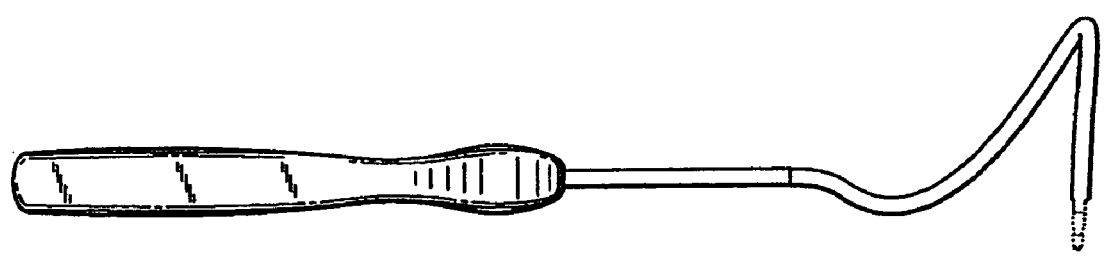
FIG. 40 is a top view of the instrument of FIG. 39.
Figure 41:
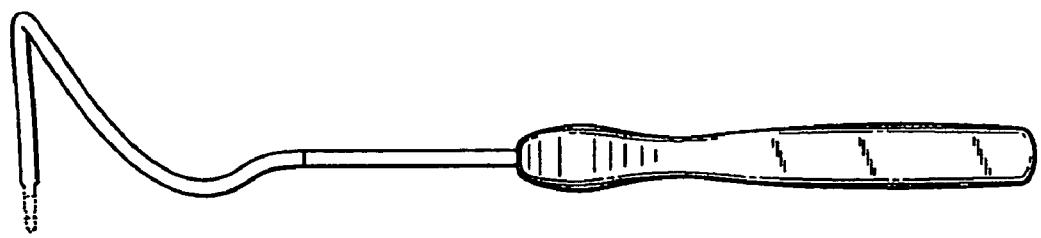
FIG. 41 is a bottom view of the instrument of FIG. 39.
Figure 42:
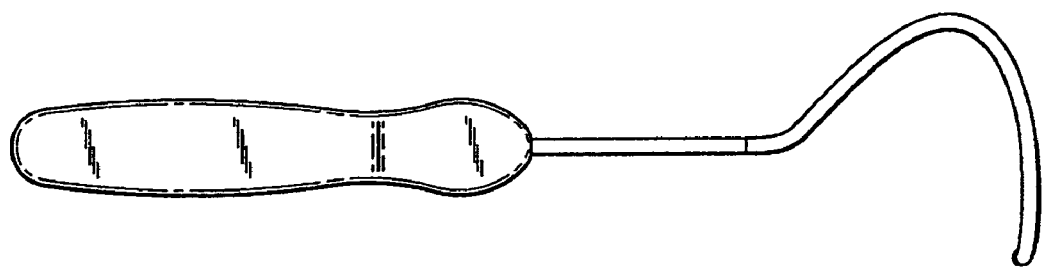
FIG. 42 is a front view of the instrument of FIG. 39.
Figure 43:
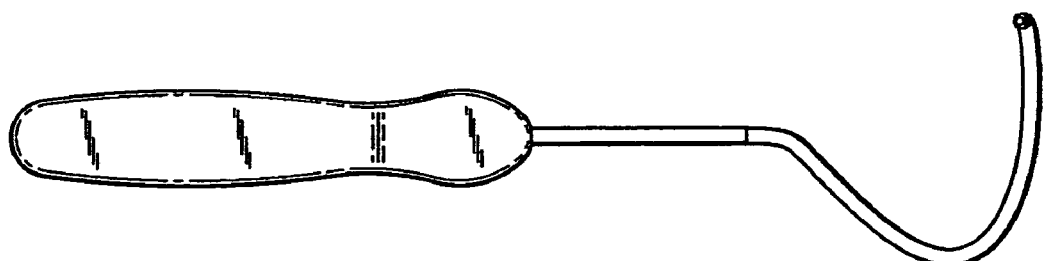
FIG. 43 is a rear view of the instrument of FIG. 39.
Figure 44:
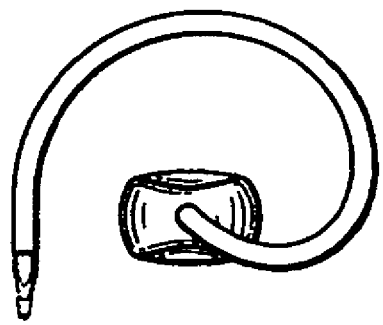
FIG. 44 is a right end view of the instrument of FIG. 39.
Figure 45:
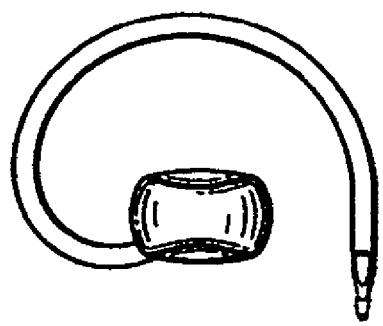
FIG. 45 is a left end view of the instrument of FIG. 39.
Figure 46:
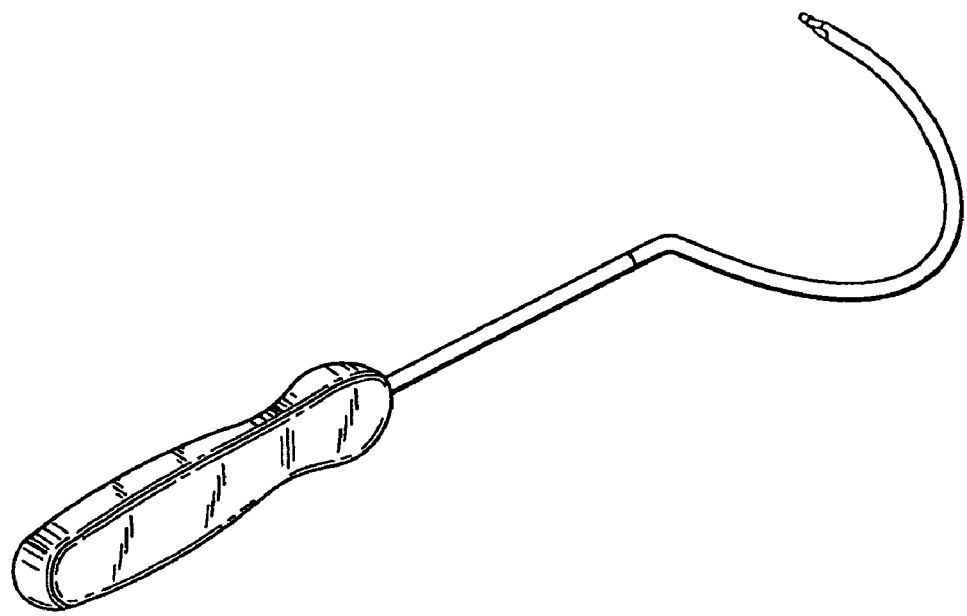
FIG. 46 is a perspective view of a design of a instrument according to another aspect of the present invention.
Figure 47:
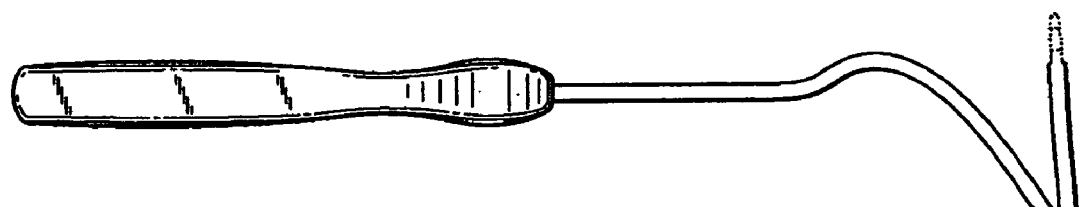
FIG. 47 is a top view of the instrument of FIG. 46.
Figure 48:
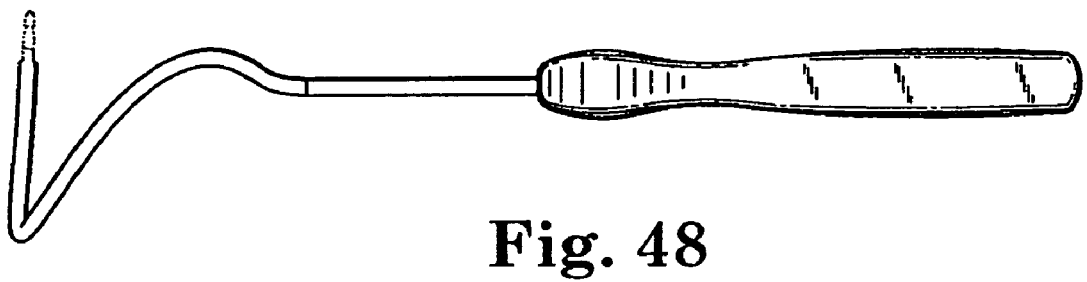
FIG. 48 is a bottom view of the instrument of FIG. 46.
Figure 49:
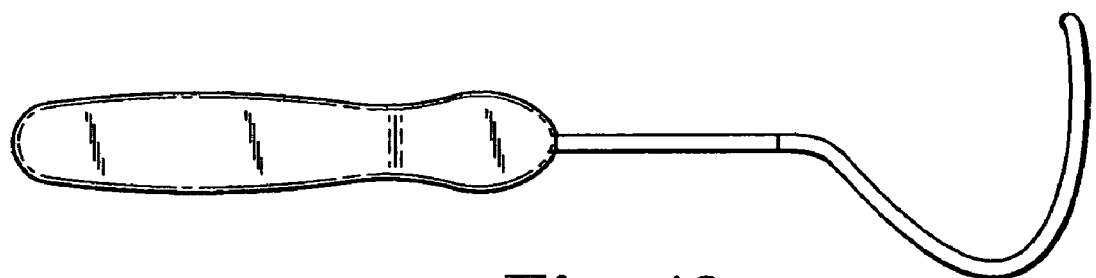
FIG. 49 is a front view of the instrument of FIG. 46.
Figure 50:
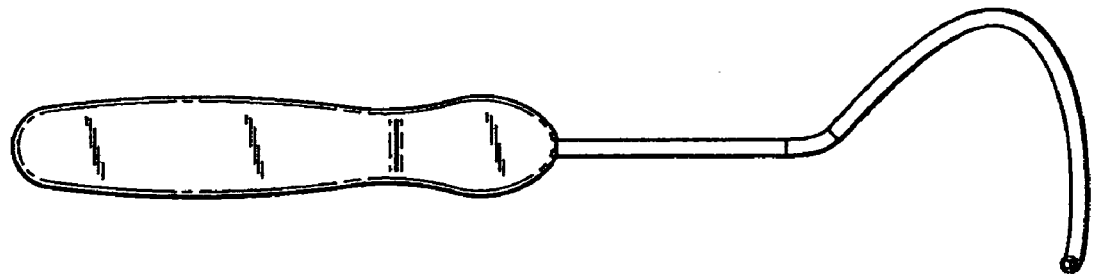
FIG. 50 is a rear view of the instrument of FIG. 46.
Figure 51:
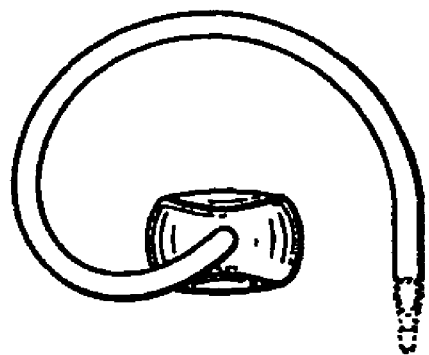
FIG. 51 is a right end view of the instrument of FIG. 46.
Figure 52:
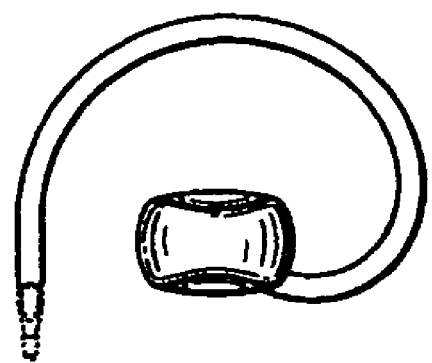
FIG. 52 is a left end view of the instrument of FIG. 46.

The surgeon then pulls the assembly through the lateral incision. This is shown for the left side of the patient's body in FIG. 37. Next the surgeon cuts the sling mesh just below the level of the connector and discards the needle and dilator. In FIG. 38, this has been accomplished for the portion of the system on the right side of the patient's body.

The surgeon preferably keeps the centering marks on the plastic sheath in the midline. This is repeated on the contralateral side.

If vaginal retraction has been used, it should be removed to adjust the tension of the sling. The sling may be finely tensioned by placing a blunt instrument (e.g. a Metzenbaum scissors or small instrument) between the sling and urethra.

The surgeon removes the plastic protective sheaths 44A and discards them.

Under spinal or regional anesthesia, the position of the sling can be improved by the cough test after filling up the bladder, at the discretion of the surgeon.

To loosen the mesh, the surgeon place an instrument (e.g. Metzenbaum clamp) between the sling mesh and the urethra. The surgeon ensures that both the mesh and the tensioning suture are located beneath the clamp. The clamp may be used to pull down and loosen the sling mesh as desired.

To tighten the sling mesh, the surgeon places a clamp (e.g. hemostat) across the sling mesh at the lateral incisions 400. The surgeon ensures that both the tensioning suture and the complete width of the sling are captured within the clamp. The sling mesh may be rolled around the clamp to improve the grip. The surgeon pulls up to tighten the sling mesh as desired. If needed, this can be repeated on the contralateral side.

To complete the procedure, the surgeon trims the sling mesh at the level of the subcutaneous tissue. A multi-layer closure of the vaginal incision and the skin incisions may then be completed.

All patents, patent applications, and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating urinary incontinence in a male patient comprising the steps of:
   (a) creating a first incision in a position below the male patient's urethra and a pair of pelvic incisions, wherein the pelvic incisions are substantially aligned with the male patient's obturator foramen;
   (b) providing an elongate surgical instrument and an elongate implant for treating urinary incontinence;
   (c) passing one of the ends of the instrument through one obturator foramen via one of the pelvic incisions;
   (d) associating the implant with the instrument;
   (e) using the instrument to pass the implant through a tissue of the first incision and the one pelvic incision such that the implant extends through the one obturator foramen and one of the pelvic incisions.

2. The method of claim 1 wherein the incisions are made with the patient placed in a modified lithotomy position.

3. The method of claim 1 wherein the instrument passes through an obturator foramen membrane adjacent to a medial region of the obturator foramen membrane inferior to a region of the patient's obturator foramen containing vascular and nerve structures.

4. The method of claim 1 wherein one end of the instrument passes through an obturator foramen membrane adjacent to the patient's lateral margins of each ischiopubic ramus.

5. The method of claim 1 wherein an end of the instrument is inserted into the first incision and is passed from the first incision through an obturator foramen and then to the pelvic incision.

6. The method of claim 1 wherein an end of the instrument passes from at least one of the pelvic incisions through one of the obturator foramen and medially to the first incision.

7. The method of claim 1 wherein the implant provides support for the patient's urethra.

8. The method of claim 1 wherein at least one end of the instrument comprises an eyelet to associate the instrument with the implant.

9. The method of claim 1 wherein at least one end of the instrument is associated with the implant using a connector.

10. The method of claim 1 wherein the implant is a sling.

11. The method of claim 1 wherein the implant is a polymer fiber sling.

12. The method of claim 1 wherein the implant is a fabric structure configured as a sling.

13. The method of claim 1 comprising;
(f) passing one of the ends of the instrument though the other obturator foramen and the other pelvic incision; and
(g) using the instrument to extend the implant though the first incision and the other obturator foramen to the other pelvic incision such that the implant then extends from one pelvic incision to the other pelvic incision, through both obturator foramen and adjacent to the male patient's urethra and bladder.

14. The method of claim 1 comprising:
(a) creating a first incision in a position below the male patient's urethra and a pair of pelvic incisions, wherein the pelvic incisions are substantially aligned with the patient's obturator foramen;
(b) providing:
a first surgical instrument for use on a right side of a patient, the first surgical instrument comprising a handle portion and a needle portion having substantial structure in thee dimensions and a distal end, the needle portion having a portion that is sized and shaped to extend between a pelvic incision on a right side of the patient and the first incision below the patient's urethra,
a second surgical instrument for use on a left side of a patient, the second surgical instrument comprising a handle portion and a needle portion having substantial structure in thee dimensions and a distal end, the needle portion having a portion that is sized and shaped to extend between a pelvic incision on a left side of the patient and the first incision below the patient's urethra, and
an elongate implant;
(c) passing the end of the first surgical instrument through the patient's right obturator foramen via the pelvic incision on the right side of the patient;

(d) associating the implant with the first surgical instrument;
(e) using the first surgical instrument to pass the implant through the first incision and the pelvic incision on the right side of the patient such that the implant extends through the right obturator foramen and the pelvic incision on the right side of the patient;
(f) passing the end of the second surgical instrument through the patient's left obturator foramen and the pelvic incision on the left side of the patient;
(g) using the second surgical instrument to extend the implant through the first incision and the left obturator foramen to the pelvic incision on the left side of the patient; and
(h) extending the implant from one pelvic incision to the other pelvic incision, through both obturator foramen and adjacent to the patient's urethra and bladder.

15. A method according to claim 14 wherein the needle portion having substantial structure in three dimensions of the first instrument comprises a variable spiral portion, and the needle portion having substantial structure in three dimensions of the second instrument comprises a variable spiral portion.

16. A method according to claim 14 wherein the needle portion having substantial structure in three dimensions of the first instrument comprises a variable helix, and the needle portion having substantial structure in three dimensions of the second instrument comprises a variable helix.

17. A method according to claim 14 wherein:
the elongate implant comprises a mid-portion and two opposing end portions, each end portion comprises a sheath and a connector at a distal end, and
each connecter is configured to mate with an end of a needle to produce a substantially permanent attachment between the connector and the end of the needle.

18. A method according to claim 17 wherein each end portion comprises a suture extending along a length of the end portion.

19. A method according to claim 14 wherein the elongate implant comprises a mid-portion and two opposing end portions and each end portion comprises a suture extending a along length of the end portion.

20. A method according to claim 17 wherein the attachment between the needles and the connector is a substantially permanent snap fit attachment.

21. The method of claim 14 wherein the instruments pass through an obturator foramen membrane adjacent to a medial region of the obturator foramen membrane inferior to a region of the patient's obturator foramen containing vascular and nerve structures.

22. The method of claim 14 wherein one end of each instrument passes through an obturator foramen membrane adjacent to the patient's lateral margins of each ischiopubic ramus.

23. The method of claim 14 wherein an end of each instrument passes from at least one of the pelvic incisions through one of the obturator foramen and medially to the first incision.

24. The method of claim 1 wherein the elongate implant comprises a mid-portion and two opposing end portions, and the mid-portion has a width that is greater than a width of the end portions.

25. The method of claim 13 wherein the elongate implant comprises a mid-portion and two opposing end portions, and the mid-portion has a width that is greater than a width of the end portions.

26. The method of claim 17 wherein the elongate implant comprises a mid-portion and two opposing end portions, and the mid-portion has a width that is greater than a width of the end portions.

27. The method of claim 14 wherein the end of the first surgical instrument is inserted into the first incision and is further inserted to pass from the first incision through the patient's right obturator foramen and then to the pelvic incision on the right side of the patient, and the end of the second surgical instrument is inserted into the first incision and is further inserted to pass from the first incision through the patient's left obturator foramen and then to the pelvic incision on the left side of the patient.

28. The method of claim 1 wherein the elongate implant comprises a mid-portion and two opposing end portions, and each end portion comprises a sheath extending along a length of the end portion.

29. The method of claim 28 comprising, after the implant is passed through tissue to extend from the first pelvic incision to the second pelvic incision, through both obturator foramen and adjacent to the patient's urethra, the method comprises adjusting the placement of the implant below the urethra by moving an end portion and sheath within the tissue, followed by removing the sheath from the end portion.

30. The method of claim 14 wherein the elongate implant comprises a mid-portion and two opposing end portions, and each end portion comprises a sheath extending along a length of the end portion.

31. A method according to claim 30 comprising, after the implant is passed through tissue to extend from the pelvic incision in the right side of the patient to the pelvic incision on the left side of the patient, through both obturator foramen and adjacent to the patient's urethra, the method comprises adjusting the placement of the implant below the urethra by moving an end portion and sheath within the tissue, followed by removing the sheath from the end portion.

* * * * *